(12) United States Patent
Baxter et al.

(10) Patent No.: US 7,498,338 B2
(45) Date of Patent: Mar. 3, 2009

(54) COMPOUNDS

(75) Inventors: Andrew Baxter, Loughborough (GB); Nafizal Hossain, Lund (SE); Svetlana Ivanova, Lund (SE); Marguerite Mensonides-Harsema, Lund (SE); Austen Pimm, Loughborough (GB); James Reuberson, Loughborough (GB)

(73) Assignee: AstraZeneca AB (SE)

( * ) Notice: Subject to any disclaimer, the term of this patent is extended or adjusted under 35 U.S.C. 154(b) by 253 days.

(21) Appl. No.: 10/579,545

(22) PCT Filed: Nov. 15, 2004

(86) PCT No.: PCT/SE2004/001658

§ 371 (c)(1), (2), (4) Date: May 16, 2006

(87) PCT Pub. No.: WO2005/049620

PCT Pub. Date: Jun. 2, 2005

(65) Prior Publication Data

US 2007/0129393 A1    Jun. 7, 2007

(30) Foreign Application Priority Data

Nov. 20, 2003    (SE)    .................................... 0303090

(51) Int. Cl.
*A61K 31/438* (2006.01)
*C07D 491/107* (2006.01)

(52) U.S. Cl. .......................... 514/278; 546/17; 548/409; 548/411; 544/124; 514/232.8; 514/409

(58) Field of Classification Search ................. 514/278, 514/232.8, 409; 546/17; 548/409, 411; 544/124
See application file for complete search history.

(56) References Cited

U.S. PATENT DOCUMENTS

| 4,010,201 | A | 3/1977 | Lednicer |
| 4,263,317 | A | 4/1981 | Martin et al. |
| 5,962,462 | A | 10/1999 | Mills et al. |
| 2005/0245741 | A1 | 11/2005 | Hossain et al. |
| 2006/0252751 | A1 | 11/2006 | Xue et al. |
| 2007/0021498 | A1 | 1/2007 | Hossain |
| 2007/0099945 | A1 | 5/2007 | Hossain et al. |
| 2007/0123543 | A1 | 5/2007 | Hossain et al. |
| 2007/0203229 | A1 | 8/2007 | Hossain |
| 2007/0203230 | A1 | 8/2007 | Hossain |
| 2007/0249648 | A1 | 10/2007 | Bladh et al. |

FOREIGN PATENT DOCUMENTS

| EP | 0004951 | 10/1979 |
| EP | 0004952 | 10/1979 |
| EP | 0417631 | 3/1991 |
| EP | 0722941 | 7/1996 |
| EP | 1061076 | 12/2000 |
| WO | WO 92/10096 | 6/1992 |
| WO | WO 96/36625 | 11/1996 |
| WO | WO 98/25605 | 6/1998 |
| WO | WO 98/31364 | 7/1998 |
| WO | WO 00/14086 | 3/2000 |
| WO | WO 01/30780 | 5/2001 |
| WO | WO 01/64213 A1 | 9/2001 |
| WO | WO 01/98273 | 12/2001 |
| WO | WO 02/102387 | 12/2002 |
| WO | WO 03/037271 | 5/2003 |
| WO | WO 2004/005295 A1 | 1/2004 |
| WO | WO 2004/041279 | 5/2004 |
| WO | WO 2005/037814 | 4/2005 |
| WO | WO 2005/040167 | 5/2005 |
| WO | WO 2005/049620 | 6/2005 |
| WO | WO 2005/054249 | 6/2005 |
| WO | WO 2005/061499 | 7/2005 |
| WO | WO 20005/092895 | 10/2005 |

OTHER PUBLICATIONS

Mehrotra et al., "Spirocyclic Nonpeptide Glycoprotein IIb-IIIa Antagonists. Part 3: Synthesis and SAR of Potent and Specific 2,8-Diazaspiro[4.5]decanes", Bioorganic & Medicinal Chemistry Letters 12:1103-1107 (2002).

Pujol et al., "Novel tricyclic spiropiperidines. Synthesis and adrenergic activity of spiro(1,3-benzodioxolopiperidines) and spiro(1,3-benzodioxanepiperidines)", *Eur J Med Chem* 31:889-894 (1996).

Brown et al., "Novel CCR1 antagonist with improved metabolic stability", *Bioorg. Med. Chem. Lett.* 14:2175-2179 (2004).

Chen et al., "Heterodimerization and cross-desensitization between the μ-opioid receptor and the chemokine CCR5 receptor", *Eur. J. Pharmacol.* 483:175-186 (2004).

Dorwald F.Z. *Side Reactions in Organic Synthesis*. Wiley: VCH, Weinheim, 2005. p. IX of Preface.

Godessart N., "Chemokine Receptors: Attractive Targets for Drug Discovery", *Ann N.Y. Acad. Sci.* 1051:647-657 (2005).

(Continued)

*Primary Examiner*—Charanjit S Aulakh
(74) *Attorney, Agent, or Firm*—Fish & Richardson P.C.

(57) ABSTRACT

The invention provides compounds of formula (I) wherein m, $R^1$, n, $R^2$, q, X, Y, Z, t, $R^3$, $R^4$, $R^5$, $R^6$, $R^7$ and $R^8$ are as defined in the specification, processes for their preparation, pharmaceutical compositions containing them and their use in therapy.

11 Claims, No Drawings

OTHER PUBLICATIONS

Knochel et al., "Highly Functionalized Organomagnesium Reagents Prepared through Haolgen-Metal Exchange", *Angew. Chem. Int. Ed.* 42:4302-4320 (2003).

Li J.J. "Grignard reaction." in: *Name Reactions: A Collection of Detailed Reaction Mechanisms* Third Expanded Edition Springer 2006, pp. 271-272.

Martin et al., "Do Structurally Similar Molecules Have Similar Biological Activity?", *J. Med. Chem.* 45:4350-4358 (2002).

Pozharskii et al., *Heterocycles in Life and Society.* Wiley, 1997, pp. 1-6.

Thoma et al., "Orally Bioavailable Competitive CCR5 Antagonists", *J. Med. Chem.* 47:1939-1955 (2004).

Thomson et al., *The Cytokine Handbook*, 4th ed. New York, Academic Press, 2003, pp. 1084-1087.

Ting et al., "The synthesis of substituted bipiperidine amide compounds as CCR3 ligands: Antagonists versus agonists", *Bioorg. Med. Chem. Lett.* 15:3020-3023 (2005).

Xie et al., "Identification of novel series of human CCR1 antagonists", *Bioorg. Med. Chem. Lett.* 18:2215-2221 (2008).

COMPOUNDS

CROSS-REFERENCE TO RELATED APPLICATIONS

This application is a national phase application under 35 U.S.C. §371 of PCT International Application No. PCT/SE2004/001658, filed Nov. 15, 2004, which claims priority to Swedish Application Serial No. 0303090-5, filed Nov. 20, 2003.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

In accordance with the present invention, there is therefore provided a compound of formula

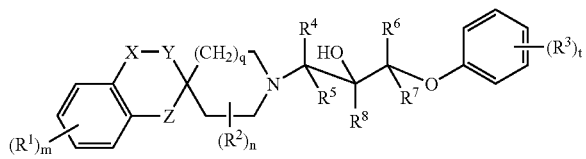

(I)

wherein
m is 0, 1, 2, 3 or 4;
each $R^1$ independently represents halogen, cyano, hydroxyl, $C_1$-$C_6$ alkyl, $C_1$-$C_6$ haloalkyl, $C_1$-$C_6$ alkoxy or sulphonamido;
X represents a bond, —$CH_2$— or —O—, Y represents a bond, —$CH_2$— or —O—, and Z represents a bond, —O—, —NH— or —$CH_2$—, provided that only one of X, Y and Z can represent a bond at any one time and provided that X and Y do not both simultaneously represent —O—;
n is 0, 1 or 2;
each $R^2$ independently represents halogen, $C_1$-$C_6$ alkyl or $C_1$-$C_6$ haloalkyl
q is 0 or 1;
t is 0, 1, 2, 3, 4 or 5;
each $R^3$ independently represents halogen, cyano, nitro, hydroxyl, —C(O)H, —$NR^9R^{10}$, —$CH_2C(O)NR^{11}R^{12}$, —$CH_2NHC(O)R^{13}$, —$NHSO_2R^{14}$, —$SO_2NR^{15}R^{16}$, —$CH_2$—$R^{17}$, $C_1$-$C_6$ alkylcarbonyl, phenylcarbonyl, $C_3$-$C_6$ cycloalkyl, or a group selected from $C_1$-$C_6$ alkyl, $C_2$-$C_6$ alkenyl, $C_2$-$C_6$ alkynyl, $C_1$-$C_6$ alkoxy, phenyl and a saturated or unsaturated 5- to 10-membered heterocyclic ring system comprising at least one ring heteroatom selected from nitrogen, oxygen and sulphur, each group being optionally substituted with at least one substituent selected from halogen, cyano, hydroxyl, carboxyl, $C_1$-$C_6$ alkyl, $C_1$-$C_6$ alkoxy and $C_1$-$C_6$ alkoxycarbonyl;
$R^4$, $R^5$, $R^6$, $R^7$ and $R^8$ each independently represent hydrogen, halogen, $C_1$-$C_6$ alkyl or $C_1$-$C_6$ haloalkyl;
$R^9$ and $R^{10}$ each independently represent hydrogen or $C_1$-$C_6$ alkyl;
$R^{11}$ and $R^{12}$ each independently represent hydrogen or $C_1$-$C_6$ alkyl, or $R^{11}$ and $R^{12}$ together with the nitrogen atom to which they are attached form a 4- to 7-membered saturated heterocyclic ring which may be optionally substituted with at least one substituent selected from hydroxyl;
$R^{13}$ and $R^{14}$ each independently represent hydrogen or $C_1$-$C_6$ alkyl; and
$R^{15}$ and $R^{16}$ each independently represent hydrogen or $C_1$-$C_6$ alkyl, or $R^{15}$ and $R^{16}$ together with the nitrogen atom to which they are attached form a 4- to 7-membered saturated heterocyclic ring which may be optionally substituted with at least one substituent selected from hydroxyl;
$R^{17}$ is a 5 to 7-membered saturated heterocyclic ring containing at least one nitrogen atom, which ring may be optionally substituted with one or more oxo groups;

or a pharmaceutically acceptable salt or solvate thereof.

In the context of the present specification, unless otherwise stated, an alkyl, alkenyl or alkynyl substituent group or moiety in a substituent group may be linear or branched. A haloalkyl substituent group will comprise at least one halogen atom, e.g. one, two, three or four halogen atoms. In the ring substituted by $R^2$, $R^2$ may be attached to any suitable ring carbon atom including the carbon atom of $(CH_2)_q$. Also, in the definition of $R^3$, it should be understood that the saturated or unsaturated 5- to 10-membered heterocyclic ring system may have alicyclic or aromatic properties. An unsaturated ring system will be partially or fully unsaturated. Further, when $R^{11}$ and $R^{12}$ or $R^{15}$ and $R^{16}$ represent a 4- to 7-membered saturated heterocyclic ring, it should be understood that the only heteroatom present is the nitrogen atom to which $R^{11}$ and $R^{12}$, or $R^{15}$ and $R^{16}$ are attached.

In an embodiment of the invention, m is 0 or 1, particularly 1.

Each $R^1$ independently represents halogen (e.g. chlorine, fluorine, bromine or iodine), cyano, hydroxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, haloalkyl (e.g. trifluoromethyl or pentafluoroethyl), $C_1$-$C_6$, preferably $C_1$-$C_4$, alkoxy (e.g. methoxy, ethoxy, n-propoxy or n-butoxy) or sulphonamido.

In an embodiment of the invention, each $R^1$ independently represents halogen, $C_1$-$C_6$, preferably $C_1$-$C_4$, alkyl or $C_1$-$C_6$, preferably $C_1$-$C_4$, haloalkyl.

In another embodiment, each $R^1$ independently represents fluorine, chlorine, methyl or trifluoromethyl, particularly chlorine.

Combinations of X and Y of particular interest include any one or more of the following:

| X | Y |
|---|---|
| bond | O |
| O | bond |
| $CH_2$ | bond |
| bond | $CH_2$ |
| $CH_2$ | O |
| O | $CH_2$ |
| $CH_2$ | $CH_2$ |

In an embodiment of the invention, X and Y have the meanings shown below:

| X | Y |
|---|---|
| bond | O |
| O | bond |
| $CH_2$ | bond |
| bond | $CH_2$ |

Combinations of X, Y and Z of particular interest include any one or more of the following:

| X | Y | Z |
|---|---|---|
| bond | O | $CH_2$ |
| O | bond | $CH_2$ |
| $CH_2$ | bond | O |
| bond | $CH_2$ | O |
| $CH_2$ | O | bond |
| $CH_2$ | $CH_2$ | bond |

In an embodiment of the invention, Z represents —O— or —$CH_2$—.

In an embodiment of the invention, X, Y and Z have the meanings shown below:

| X | Y | Z |
|---|---|---|
| bond | O | $CH_2$ |
| O | bond | $CH_2$ |
| $CH_2$ | bond | O |
| bond | $CH_2$ | O |

Each $R^2$ independently represents halogen (e.g. chlorine, fluorine, bromine or iodine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) or $C_1$-$C_6$, preferably $C_1$-$C_4$, haloalkyl (e.g. trifluoromethyl or pentafluoroethyl).

In an embodiment of the invention, n is 0 or n is 1 and $R^2$ represents halogen, particularly fluorine.

In an embodiment of the invention, t is 0 or 1 or 2 or 3 or 4 or 5 or a combination of two or more thereof.

In another embodiment, t is 1, 2 or 3.

Each $R^3$ independently represents halogen (e.g. chlorine, fluorine, bromine or iodine), cyano, nitro, hydroxyl, —C(O)H, —$NR^9R^{10}$, —$CH_2C(O)NR^{11}R^{12}$, —$CH_2NHC(O)R^{13}$, —$NHSO_2R^{14}$, —$SO_2NR^{15}R^{16}$, —$CH_2$—$R^{17}$, $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, isobutylcarbonyl, tert-butylcarbonyl, n-pentylcarbonyl or n-hexylcarbonyl), phenylcarbonyl, $C_3$-$C_6$, preferably $C_5$-$C_6$, cycloalkyl (cyclopropyl, cyclobutyl, cyclopentyl or cyclohexyl), or a group selected from $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_2$-$C_6$, preferably $C_2$-$C_4$, alkenyl (e.g. ethenyl, prop-1-enyl, prop-2-enyl, but-1-enyl, pent-1-enyl, hex-1-enyl or 2-methyl-pent-2-enyl), $C_2$-$C_6$, preferably $C_2$-$C_4$, alkynyl (e.g. ethynyl, prop-1-ynyl, prop-2-ynyl, but-1-ynyl, pent-1-ynyl, penta-1,3-diynyl or hex-1-ynyl), $C_1$-$C_6$, preferably $C_1$-$C_4$, alkoxy (e.g. methoxy, ethoxy, n-propoxy, isopropoxy, n-butoxy, isobutoxy, tert-butoxy, n-pentoxy or n-hexoxy), phenyl and a saturated or unsaturated 5- to 6-, 7-, 8-, 9- or 10-membered heterocyclic ring system comprising at least one ring heteroatom (e.g. one, two, three or four ring heteroatoms independently) selected from nitrogen, oxygen and sulphur, each group being optionally substituted with at least one substituent (e.g. one, two, three or four substituents independently) selected from halogen (e.g. chlorine, fluorine, bromine or iodine), cyano, hydroxyl, carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy, n-butoxy, isobutoxy, tert-butoxy, n-pentoxy or n-hexoxy) and $C_1$-$C_6$, preferably $C_1$-$C_4$, alkoxycarbonyl (e.g. methoxycarbonyl, ethoxycarbonyl, n-propoxycarbonyl, isopropoxycarbonyl, n-butoxycarbonyl, isobutoxycarbonyl, tert-butoxycarbonyl, n-pentoxycarbonyl or n-hexoxycarbonyl).

The saturated or unsaturated 5- to 10-membered heterocyclic ring system in $R^3$ may be monocyclic or polycyclic (e.g. bicyclic), examples of which include pyrrolidinyl, morpholinyl, piperidinyl, pyrazolyl, thiazolidinyl, thienyl, isoxazolyl, thiadiazolyl, oxadiazolyl, pyrrolyl, furanyl, thiazolyl, indolyl, quinolinyl, benzimidazolyl, triazolyl, tetrazolyl, pyridinyl and combinations of any two or more thereof.

In an embodiment of the invention, each $R^3$ independently represents halogen, cyano, nitro, hydroxyl, —C(O)H, —$NR^9R^{10}$, —$CH_2C(O)NR^{11}R^{12}$, $CH_2NHC(O)R^{13}$, —$NHSO_2R^{14}$, —$SO_2NR^{15}R^{16}$, —$CH_2$—$R^{17}$, $C_1$-$C_4$ alkylcarbonyl, phenylcarbonyl, $C_5$-$C_6$ cycloalkyl or a group selected from $C_1$-$C_4$ alkyl, $C_2$-$C_4$ alkenyl, $C_2$-$C_4$ alkynyl, $C_1$-$C_4$ alkoxy, phenyl and a saturated or unsaturated 5- to 6-membered heterocyclic ring system comprising at least one ring heteroatom (e.g. one, two, three or four ring heteroatoms independently) selected from nitrogen, oxygen and sulphur (such as isoxazolyl, pyrrolyl, morpholinyl, piperidinyl or oxadiazolyl), each group being optionally substituted with at least one substituent (e.g. one, two, three or four substituents independently) selected from halogen, cyano, hydroxyl, carboxyl, $C_1$-$C_4$ alkyl, $C_1$-$C_4$ alkoxy and $C_1$-$C_4$ alkoxycarbonyl.

In an embodiment of the invention, each $R^3$ independently represents halogen, cyano, nitro, hydroxyl, —C(O)H, —$NR^9R^{10}$, —$CH_2C(O)NR^{11}R^{12}$, —$CH_2NHC(O)R^{13}$— $NHSO_2R^{14}$, —$SO_2NR^{15}R^{16}$, $C_1$-$C_4$ alkylcarbonyl, phenylcarbonyl, $C_5$-$C_6$ cycloalkyl or a group selected from $C_1$-$C_4$ alkyl, $C_2$-$C_4$ alkenyl, $C_2$-$C_4$ alkynyl, $C_1$-$C_4$ alkoxy, phenyl and a saturated or unsaturated 5- to 6-membered heterocyclic ring system comprising at least one ring heteroatom (e.g. one, two, three or four ring heteroatoms independently) selected from nitrogen, oxygen and sulphur (such as isoxazolyl, pyrrolyl, morpholinyl, piperidinyl or oxadiazolyl), each group being optionally substituted with at least one substituent (e.g. one, two, three or four substituents independently) selected from halogen, cyano, hydroxyl, carboxyl, $C_1$-$C_4$ alkyl, $C_1$-$C_4$ alkoxy and $C_1$-$C_4$ alkoxycarbonyl.

In another embodiment, each $R^3$ independently represents fluorine, chlorine, bromine, cyano, nitro, hydroxyl, —C(O)H, —$NR^9R^{10}$, —$CH_2C(O)NR^{11}R^{12}$, —$CH_2NHC(O)R^{13}$, —$NHSO_2R^{14}$, —$CH_2$—$R^{17}$, methylcarbonyl, ethylcarbonyl, phenylcarbonyl, cyclohexyl, or a group selected from $C_1$-$C_4$ alkyl, ethenyl, ethynyl, methoxy, ethoxy, phenyl and a saturated or unsaturated 5- to 6-membered heterocyclic ring system comprising one, two or three ring heteroatoms independently selected from nitrogen and oxygen (such as isoxazolyl, pyrrolyl, morpholinyl, piperidinyl or oxadiazolyl), each group being optionally substituted with one, two or three substituents independently selected from halogen (particularly fluorine), hydroxyl, $C_1$-$C_4$ alkyl (particularly $C_1$-$C_2$ alkyl) and $C_1$-$C_2$ alkoxycarbonyl.

$R^4$, $R^5$, $R^6$, $R^7$ and $R^8$ each independently represent hydrogen, halogen (e.g. chlorine, fluorine, bromine or iodine), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) or $C_1$-$C_6$, preferably $C_1$-$C_4$, haloalkyl (e.g. trifluoromethyl or pentafluoroethyl).

In an embodiment of the invention, $R^4$, $R^5$, $R^6$, $R^7$ and $R^8$ each independently represent a hydrogen atom or a methyl group.

In another embodiment of the invention, $R^4$, $R^5$, $R^6$ and $R^7$ each represent a hydrogen atom and $R^8$ represents a methyl group.

In an embodiment of the invention, $R^4$, $R^5$, $R^6$, $R^7$ and $R^8$ each represent a hydrogen atom.

$R^9$ and $R^{10}$ each independently represent hydrogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl).

In an embodiment of the invention, $R^9$ and $R^{10}$ each represent hydrogen.

$R^{11}$ and $R^{12}$ each independently represent hydrogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $R^{11}$ and $R^{12}$ together with the nitrogen atom to which they are attached form a 4 to 7-membered saturated heterocyclic ring (e.g. pyrrolidinyl or piperidinyl) which may be optionally substituted with at least one substituent (e.g. one, two or three substituents independently) selected from hydroxyl.

In an embodiment of the invention, $R^{11}$ and $R^{12}$ each independently represent hydrogen or $C_1$-$C_4$ alkyl, or $R^{11}$ and $R^{12}$ together with the nitrogen atom to which they are attached form a 5- to 6-membered saturated heterocyclic ring which may be optionally substituted with one or two hydroxyl groups.

In another embodiment, $R^{11}$ and $R^{12}$ each independently represent hydrogen or $C_1$-$C_2$ alkyl, or $R^{11}$ and $R^{12}$ together with the nitrogen atom to which they are attached form a 5-membered saturated heterocyclic ring which may be optionally substituted with one hydroxyl group.

$R^{13}$ and $R^{14}$ each independently represent hydrogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), particularly methyl.

$R^{15}$ and $R^{16}$ each independently represent hydrogen or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), or $R^{15}$ and $R^{16}$ together with the nitrogen atom to which they are attached form a 4- to 7-membered saturated heterocyclic ring (e.g. pyrrolidinyl or piperidinyl) which may be optionally substituted with at least one substituent (e.g. one, two or three substituents independently) selected from hydroxyl.

$R^{17}$ is a 5 to 7-membered saturated heterocyclic ring containing at least one (e.g. one or two) nitrogen atom, which ring may be optionally substituted with one or more (e.g. 1 or two) oxo groups. In an embodiment, $R^{17}$ is a 5 to 7-membered saturated heterocyclic ring containing 2 nitrogen atoms and which ring is substituted by two oxo groups (e.g. imidazoline-2,4-dione).

In an embodiment of the invention:
m is 0, 1, 2, 3 or 4;
each $R^1$ independently represents halogen, cyano, hydroxyl, $C_1$-$C_6$ alkyl, $C_1$-$C_6$ haloalkyl, $C_1$-$C_6$ alkoxy or sulphonamido (—$SO_2NH_2$);
X represents a bond, —$CH_2$— or —O—, Y represents a bond, —$CH_2$— or —O—, and Z is represents a bond, —O—, —NH— or —$CH_2$—, provided that only one of X, Y and Z can represent a bond at any one time and provided that X and Y do not both simultaneously represent —O—;
n is 0, 1 or 2;
each $R^2$ independently represents halogen, $C_1$-$C_6$ alkyl or $C_1$-$C_6$ haloalkyl;
q is 0 or 1;
t is 0, 1, 2, 3, 4 or 5;
each $R^3$ independently represents halogen, cyano, nitro, hydroxyl, —C(O)H, —$NR^9R^{10}$, —$CH_2C(O)NR^{11}R^{12}$, —$CH_2NHC(O)R^{13}$, —$NHSO_2R^{14}$, —$SO_2NR^{15}R^{16}$, $C_1$-$C_6$ alkylcarbonyl, phenylcarbonyl, $C_3$-$C_6$ cycloalkyl, or a group selected from $C_1$-$C_6$ alkyl, $C_2$-$C_6$ alkenyl, $C_2$-$C_6$ alkynyl, $C_1$-$C_6$ alkoxy, phenyl and a saturated or unsaturated 5- to 10-membered heterocyclic ring system comprising at least one ring heteroatom selected from nitrogen, oxygen and sulphur, each group being optionally substituted with at least one substituent selected from halogen, cyano, hydroxyl, carboxyl, $C_1$-$C_6$ alkyl, $C_1$-$C_6$ alkoxy and $C_1$-$C_6$ alkoxycarbonyl;
$R^4$, $R^5$, $R^6$, $R^7$ and $R^8$ each independently represent hydrogen, halogen, $C_1$-$C_6$ alkyl or $C_1$-$C_6$ haloalkyl;
$R^9$ and $R^{10}$ each independently represent hydrogen or $C_1$-$C_6$ alkyl;
$R^{11}$ and $R^{12}$ each independently represent hydrogen or $C_1$-$C_6$ alkyl, or $R^{11}$ and $R^{12}$ together with the nitrogen atom to which they are attached form a 4- to 7-membered saturated heterocyclic ring which may be optionally substituted with at least one substituent selected from hydroxyl;
$R^{13}$ and $R^{14}$ each independently represent hydrogen or $C_1$-$C_6$ alkyl; and
$R^{15}$ and $R^{16}$ each independently represent hydrogen or $C_1$-$C_6$ alkyl, or $R^{15}$ and $R^{16}$ together with the nitrogen atom to which they are attached form a 4- to 7-membered saturated heterocyclic ring which may be optionally substituted with at least one substituent selected from hydroxyl;

or a pharmaceutically acceptable salt or solvate thereof.
In an embodiment of the invention:
m is 1;
$R^1$ represents halogen (particularly chlorine);

X represents a bond, —CH₂— or —O—, Y represents a bond, —CH₂— or —O— and Z represents —CH₂— or —O—, provided that X, Y and Z are different to one another;

n is 0;

q is 1;

t is 0, 1, 2, 3, 4 or 5;

each $R^3$ independently represents fluorine, chlorine, bromine, cyano, nitro, hydroxyl, —C(O)H, —NR⁹R¹⁰, —CH₂C(O)NR¹¹R¹², —CH₂NHC(O)R¹³, —NHSO₂R¹⁴, —CH₂—R¹⁷, methylcarbonyl, ethylcarbonyl, phenylcarbonyl, cyclohexyl, or a group selected from $C_1$-$C_4$ alkyl, ethenyl, ethynyl, methoxy, ethoxy, phenyl and a saturated or unsaturated 5- to 6-membered heterocyclic ring system comprising one, two or three ring heteroatoms independently selected from nitrogen and oxygen, each group being optionally substituted with one or two substituents independently selected from halogen (particularly fluorine), hydroxyl, $C_1$-$C_2$ alkyl and $C_1$-$C_2$ alkoxycarbonyl;

$R^4$, $R^5$, $R^6$, $R^7$ and $R^8$ each independently represent hydrogen;

$R^9$ and $R^{10}$ each independently represent hydrogen;

$R^{11}$ and $R^{12}$ each independently represent hydrogen or methyl, or $R^{11}$ and $R^{12}$ together with the nitrogen atom to which they are attached form a 5-membered saturated heterocyclic ring which may be optionally substituted with one hydroxyl group;

$R^{13}$ and $R^{14}$ each independently represent methyl; and $R^{17}$ is a 5 to 7-membered saturated heterocyclic ring containing 2 nitrogen atoms and which ring is substituted by two oxo groups.

Examples of compounds of the invention include:

(2S)-1-(5-Chloro-1'H,3H-spiro[1-benzofuran-2,4'-piperidin]-1'-yl)-3-(2-methoxyphenoxy)propan-2-ol hydrochloride, 2-{[(2S)-3-(5-Chloro-1'H,3H-spiro[1-benzofuran-2,4'-piperidin]-1'-yl)-2-hydroxypropyl]oxy}phenol, (2S)-1-(5-Chloro-1'H,3H-spiro[1-benzofuran-2,4'-piperidin]-1'-yl)-3-[2-(2-hydroxyethoxy)phenoxy]propan-2-ol hydrochloride, 2-(2-{[(2S)-3-(5-Chloro-1'H,3H-spiro[1-benzofuran-2,4'-piperidin]-1'-yl)-2-hydroxypropyl]oxy}phenyl)-N-methylacetate trifluoroacetate (salt), (3S)-1-[(2-{[(2S)-3-(5-Chloro-1'H,3H-spiro[1-benzofuran-2,4'-piperidin]-1'-yl)-2-hydroxypropyl]oxy}phenyl)acetyl]pyrrolidin-3-ol, N-2-{[(2S)-3-(5-Chloro-1'H,3H-spiro[1-benzofuran-2,4'-piperidin]-1'-yl-2-hydroxypropyl]oxy}benzyl)acetamide, 2-(2-{[(2S)-3-(5-Chloro-1'H,3H-spiro[1-benzofuran-2,4'-piperidin]-1'-yl)-2-hydroxypropyl]oxy}4-methoxyphenyl)-N-methylacetamide, 2-(2-{[(2S)-3-(5-Chloro-1'H,3H-spiro[1-benzofuran-2,4'-piperidin]-1'-yl)-2-hydroxypropyl]oxy})hydroxyphenyl)-N-methylacetamide trifluoroacetate (salt), 2-(4-{[(2S)-3-(5-Chloro-1'H,3H-spiro[1-benzofuran-2,4'-piperidin]-1'-yl)-2-hydroxypropyl]oxy}-2-methoxyphenyl)-N-methylacetamide, (2S)-1-(2-Amino-5-methoxyphenoxy)-3-(5-chloro-1'H,3H-spiro[1-benzofuran-2,4'-piperidin]-1'-yl)propan-2-ol bis(trifluoroacetate), N-(2-{[(2S)-3-(5-Chloro-1'H,3H-spiro[1-benzofuran-2,4'-piperidin]-1'-yl)-2-hydroxypropyl]oxy}-4-hydroxyphenyl)methanesulfonamide trifluoroacetate, N-(2-{[(2S)-3-(5-Chloro-1'H,3H-spiro[1-benzofuran-2,4'-piperidin]-1'-yl)-2-hydroxypropyl]oxy}methoxyphenyl)methanesulfonamide trifluoroacetate, (2S)-1-(4-Bromo-2-fluorophenoxy)-3-(5-chloro-1'H,3H-spiro[1-benzofuran-2,4'-piperidin]-1'-yl)propan-2-ol, (2S)-1-(5-Chloro-1'H,3H-spiro[1-benzofuran-2,4'-piperidin]-1'-yl)-3-(3-ethynylphenoxy)propan-2-ol, (2S)-1-(5-Chloro-1'H,3H-spiro[1-benzofuran-2,4'-piperidin]-1'-yl)-3-(2,4-dichloro-3,5-dimethylphenoxy)propan-2-ol, (2S)-1-(4-Chloro-2-isoxazol-5-ylphenoxy)-3-(5-chloro-1'H,3H-spiro[1-benzofuran-2,4'-piperidin]-1'-yl)propan-2-ol, (4-{[(2S)-3-(5-Chloro-1'H,3H-spiro[1-benzofuran-2,4'-piperidin]-1'-yl)-2-hydroxypropyl]oxy}phenyl)(phenyl)methanone, (2S)-1-(5-Chloro-1'H,3H-spiro[1-benzofuran-2,4'-piperidin]-1'-yl)-3-(2,3,4,6-tetrachlorophenoxy)propan-2-ol, (2S)-1-(5-Chloro-1'H,3H-spiro[1-benzofuran-2,4'-piperidin]-1'-yl)-3-(2-cyclohexyl-5-methylphenoxy)propan-2-ol, (2S)-1-(5-Chloro-1'H,3H-spiro[1-benzofuran-2,4'-piperidin]-1'-yl)-3-phenoxypropan-2-ol, (2S)-1-(2-Bromophenoxy)-3-(5-chloro-1'H,3H-spiro[1-benzofuran-2,4'-piperidin]-1'-yl)propan-2-ol, 2-{[(2S)-3-(5-Chloro-1'H,3H-spiro[1-benzofuran-2,4'-piperidin]-1'-yl)-2-hydroxypropyl]oxy}benzaldehyde, 5-tert-Butyl-2-{[(2S)-3-(5-chloro-1'H,3H-spiro[1-benzofuran-2,4'-piperidin]-1'-yl)-2-hydroxypropyl]oxy}benzaldehyde, (2S)-1-(5-Chloro-1'H,3H-spiro[1-benzofuran-2,4'-piperidin]-1'-yl)-3-1,1':3',1''-terphenyl-2'-yloxy)propan-2-ol, 1-(2-{[(2S)-3-(5-Chloro-1'H,3H-spiro[1-benzofuran-2,4'-piperidin]-1'-yl)-2-hydroxypropyl]oxy}-5-methoxyphenyl)ethanone, 1-(5-Bromo-2-{[(2S)-3-(5-chloro-1'H,3H-spiro[1-benzofuran-2,4'-piperidin]-1'-yl)-2-hydroxypropyl]oxy}phenyl)ethanone, (2S)-1-(4-Chloro-2-isopropyl-5-methylphenoxy)-3-(5-chloro-1'H,3H-spiro[1-benzofiiran-2,4'-piperidin]-1'-yl)propan-2-ol, (2S)-1-(5-Chloro-1'H,3H-spiro[1-benzofuran-2,4'-piperidin]-1'-yl)-3-(2,3-dimethyl-4-nitrophenoxy)propan-2-ol, (2S)-1-(5-Chloro-1'H,3H-spiro[1-benzofuran-2,4'-piperidin]-1'-yl)-3-(2,4-dichlorophenoxy)propan-2-ol, Ethyl (2E)-3-(4-{[(2S)-3-(5-chloro-1'H,3H-spiro[1-benzofuran-2,4'-piperidin]-1'-yl)-2-hydroxypropyl]oxy}-3-methoxyphenyl)acrylate, (2S)-1-(5-Chloro-1'H,3H-spiro[1-benzofuran-2,4'-piperidin]-1'-yl)-3-(2-methyl-3-nitrophenoxy)propan-2-ol, 5-Chloro-2-{[(2S)-3-(5-chloro-1'H,3H-spiro[1-benzofuran-2,4'-piperidin]-1'-yl)-2-hydroxypropyl]oxy}benzaldehyde, (2S)-1-(5-Chloro-1'H,3H-spiro[1-benzofuran-2,4'-piperidin]-1'-yl)-3-(2-fluorophenoxy)propan-2-ol, (2S)-1-(5-Chloro-1'H,3H-spiro[1-benzofuran-2,4'-piperidin]-1'-yl)-3-(3-fluorophenoxy)propan-2-ol, (2S)-1-(5-Chloro-1'H,3H-spiro[1-benzofuran-2,4'-piperidin]-1'-yl)-3-(4 fluorophenoxy)propan-2-ol, (2S)-1-(2-Chlorophenoxy)-3-(5-chloro-1'H,3H-spiro[1-benzofuran-2,4'-piperidin]-1'-yl)propan-2-ol, (2S)-1-(3-Chlorophenoxy)-3-(5-chloro-1'H,3H-spiro[1-benzofuran-2,4'-piperidin]-1'-yl)propan-2-ol, (2S)-1-(4-Chlorophenoxy)-3-(5-chloro-1'H,3H-spiro[1-benzofuran-2,4'-piperidin]-1'-yl)propan-2-ol, (2S)-1-(3-Bromophenoxy)-3-(5-chloro-1'H,3H-spiro[1-benzofuran-2,4'-piperidin]-1'-yl)propan-2-ol, (2S)-1-(4-Bromophenoxy)-3-(5-chloro-1'H,3H-spiro[1-benzofuran-2,4'-piperidin]-1'-yl)propan-2-ol, (2S)-1-(2-tert-Butyl-5-methylphenoxy)-3-(5-chloro-1'H,3H-spiro[1-benzofuran-2,4'-piperidin]-1'-yl)propan-2-ol, (2S)-1-(5-Chloro-1'H,3H-spiro[1-benzofuran-2,4'-piperidin]-1'-yl)-3-[2-(trifluoromethyl)phenoxy]propan-2-ol,
1-(2-{[(2S)-3-(5-Chloro-1'H,3H-spiro[1-benzofuran-2,4'-piperidin]-1'-yl)-2-hydroxypropyl]oxy}-4,5-dimethoxyphenyl)ethanone,
(2S)-1-(5-Chloro-1'H,3H-spiro[1-benzofuran-2,4'-piperidin]-1'-yl)-3-[2,3,5,6-tetrafluoro-4-(trifluoromethyl)phenoxy]propan-2-ol,
(2S)-1-(4-Chloro-3-ethylphenoxy)-3-(5-chloro-1'H,3H-spiro[1-benzofuran-2,4'-piperidin]-1'-yl)propan-2-ol,
(2S)-1-(5-Chloro-1'H,3H-spiro[1-benzofuran-2,4'-piperidin]-1'-yl)-3-[3-(2,5-dimethyl-1H-pyrol-1-yl)phenoxy]propan-2-ol,
(2S)-1-(5-Chloro-1'H,3H-spiro[1-benzofuran-2,4'-piperidin]-1'-yl)-3-[2-(hydroxymethyl)phenoxy]propan-2-ol,
(2S)-1-(5-Chloro-1'H,3H-spiro[1-benzofuran-2,4'-piperidin]-1'-yl)-3-[2-(2-hydroxyethyl)phenoxy]propan-2-ol,
3-{[(2S)-3-(5-Chloro-1'H,3H-spiro[1-benzofuran-2,4'-piperidin]-1'-yl)-2-hydroxypropyl]oxy}benzonitrile,
2-{[(2S)-3-(5-Chloro-1'H,3H-spiro[1-benzofuran-2,4'-piperidin]-1'-yl)-2-hydroxypropyl]oxy}benzonitrile,
(2S)-1-(5-Chloro-1'H,3H-spiro[1-benzofuran-2,4'-piperidin]-1'-yl)-3-(2-morpholin-4-ylphenoxy)propan-2-ol,
(2S)-1-(5-Chloro-1'H,3H-spiro[1-benzofuran-2,4'-piperidin]-1'-yl)-3-(2,3-difluoro-6-nitrophenoxy)propan-2-ol,
(2S)-1-(5-Chloro-1'H,3H-spiro[1-benzofuran-2,4'-piperidin]-1'-yl)-3-(2,3,6-trichlorophenoxy)propan-2-ol,
(2S)-1-(5-Chloro-1'H,3H-spiro[1-benzofuran-2,4'-piperidin]-1'-yl)-3-(4-fluoro-2-methoxyphenoxy)propan-2-ol,
5-Chloro-2-{[(2S)-3-(5-chloro-1'H,3H-spiro[1-benzofuran-2,4'-piperidin]-1'-yl)-2-hydroxypropyl]oxy}-3-methylbenzaldehyde,
(2S)-1-(5-Chloro-1'H,3H-spiro[1-benzofuran-2,4'-piperidin]-1'-yl)-3-[4-(4-methylpiperidin-1-yl)-2-nitrophenoxy]propan-2-ol,
(2S)-1-(5-Chloro-1'H,3H-spiro[1-benzofuran-2,4'-piperidin]-1'-yl)-3-(2,4-dichloro-3,5-dimethyl-6-nitrophenoxy)propan-2-ol,
1-(3,5-Dichloro-2-{[(2S)-3-(5-chloro-1'H,3H-spiro[1-benzofuran-2,4'-piperidin]-1'-yl)-2-hydroxypropyl]oxy}phenyl)propan-1-one,
(2S)-1-(5-Chloro-1'H,3H-spiro[1-benzofuran-2,4'-piperidin]-1'-yl)-3-(4-ethylphenoxy)propan-2-ol,
(2S)-1-(5-Chloro-1'H,3H-spiro[1-benzofuran-2,4'-piperidin]-1'-yl)-3-(2-ethylphenoxy)propan-2-ol,
(2S)-1-(5-Chloro-1'H,3H-spiro[1-benzofuran-2,4'-piperidin]-1'-yl)-3-(3-ethylphenoxy)propan-2-ol,
(2S)-1-(5-Chloro-1'H,3H-spiro[1-benzofuran-2,4'-piperidin]-1'-yl)-3-(3-morpholin-4-ylphenoxy)propan-2-ol,
(2S)-1-(5-Chloro-1'H,3H-spiro[1-benzofuran-2,4'-piperidin]-1'-yl)-3-[2-(5-methyl-1,3,4-oxadiazol-2-yl)phenoxy]propan-2-ol,
4-{[(2S)-3-(5-Chloro-1'H,3H-spiro[1-benzofuran-2,4'-piperidin]-1'-yl)-2-hydroxypropyl]oxy}benzonitrile,
(2S)-1-(5-chloro-1'H,3H-spiro[1-benzofuran-2,4'-piperidin]-1-yl)-3-[2-(pyrrolidin 1-ylsulfonyl)phenoxy]propan-2-ol,
1-(2-{[(2S)-3-(5-chloro-1'H,3H-spiro[1-benzofuran-2,4'-piperidin]-1'-yl)-2-hydroxypropoxy]benzyl}imidazoline-2,4-dione,
(2S)-{2-chloro-5-[3-(5-chloro-1'H,3H-spiro[1-benzofuran-2,4'-piperidin]-1'-yl)-2-hydroxypropoxy]phenoxy}acetic acid,
(2S)-{2,4-dichloro-5-[3-(5-chloro-1'H,3H-spiro[1-benzofuran-2,4'-piperidin]-1'-yl)-2-hydroxypropoxy]phenoxy}acetic acid, and pharmaceutically acceptable salts and solvates of any one thereof.

The present invention further provides a process for the preparation of a compound of formula (I) or a pharmaceutically acceptable salt or solvate thereof as defined above which comprises, (a) reacting a compound of formula

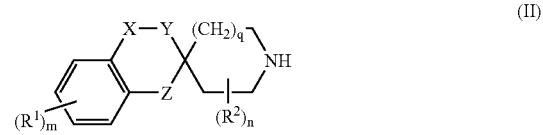

(II)

wherein m, $R^1$, n, $R^2$, q, X, Y and Z are as defined in formula (I), with a compound of formula

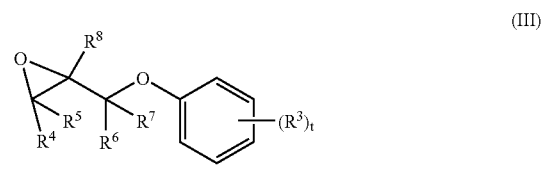

(III)

wherein t, $R^3$, $R^4$, $R^5$, $R^6$, $R^7$ and $R^8$ are as defined in formula (I); or (b) reacting a compound of formula

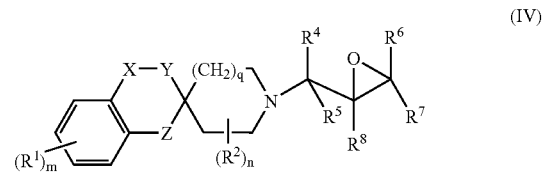

(IV)

wherein m $R^1$, n, $R^2$, q, X, Y, Z, $R^4$, $R^5$, $R^6$, $R^7$ and $R^8$ are as defined in formula (I), with a compound of formula

(V)

wherein t and $R^3$ are as defined in formula (I), in the presence of a suitable base (for example, triethylamine or potassium carbonate); or (c) when t is at least one and a group $R^3$ represents —$NHSO_2R^{14}$, reacting a compound of formula

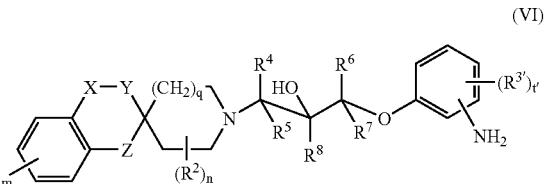

(VI)

wherein t' is 0, 1, 2, 3 or 4, $R^{3'}$ is as defined for $R^3$ in formula (I) other than —$NHSO_2R^{14}$ and m, $R^1$, n, $R^2$, q, X, Y, Z, $R^4$, $R^5$, $R^6$, $R^7$ and $R^8$ are as defined in formula (I), with a compound of formula

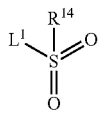

(VII)

wherein L¹ represents a leaving group (e.g. a halogen atom such as chlorine) and $R^{14}$ is as defined in formula (I), in the presence of a suitable base (for example, pyridine);
(d) where t is at least 1 and a group $R^3$ represents —$CH_2$—R17, where R17 is a 5 to 7-membered saturated heterocyclic ring containing 2 nitrogen atoms and which ring is substituted by two oxo groups, reacting a compound of formula

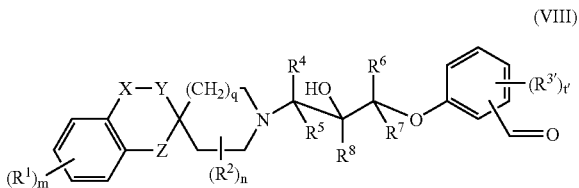

(VIII)

wherein t' is 0, 1, 2, 3 or 4, $R^{3'}$ is as defined for $R^3$ in formula (I) other than —CH2-R17, and m, $R^1$, n, $R^2$, q, X, Y, Z, $R^4$, $R^5$, $R^6$, $R^7$ and $R^8$ are as defined in formula (I), with an alkyl glycinate (for example, ethyl glycinate) in the presence of a reducing agent, (for example, $NaCNBH_4$), and subsequently with a metal isocyanate (for example, potassium isocyanate);

and optionally after (a), (b), (c) or (d) forming a pharmaceutically acceptable salt or solvate.

The processes of the invention may conveniently be carried out in a solvent, e.g. an organic solvent such as an alcohol (e.g. methanol or ethanol), a hydrocarbon (e.g. toluene) or tetrahydrofuran, dimethylformamide, N-methylpyrrolidinone, dichloromethane or acetonitrile at a temperature of, for example, 0° C. or above such as a temperature in the range from 0, 5, 10, 15 or 20° C. to 100, 110 or 120° C.

Compounds of formulae (II), (III), (IV), (V), (VI), (VII) and (VIII) are either commercially available, are known in the literature or may be prepared using known techniques.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J.W.F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemokine receptor (especially MIP-1α chemokine receptor) activity, and may be used in the treatment of autoinuune, inflammatory, proliferative and hyperproliferative diseases and immunologically-mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, eiythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease;
(7) cancers, especially non-small cell lung cancer (NSCLC) and squamous sarcoma;
(8) diseases in which angiogenesis is associated with raised chemokine levels; and
(9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease which comprises administering to a patient in need thereof a therapeutically effective amount of a compound of formula (I), or a pharmaceutically acceptable salt or solvate thereof, as hereinbefore defined.

The invention still further provides a method of treating an airways disease which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm), acetone-d$_6$ ($\delta_H$ 2.05 ppm), DMSO-d$_6$ ($\delta_H$ 2.50 ppm), or methanol-d$_4$ ($\delta_H$ 4.87 ppm) were used as internal standard. Low resolution mass spectra and accurate mass determination were recorded on a Hewlett-Packard 1100 LC-MS system equipped with APCI/ESI ionisation chambers. All solvents and commercial reagents were laboratory grade and used as received. The nomenclature used for the compounds was generated with ACD/Name and ACD/Name Batch. The abbreviations or terms used in the examples have the following meanings:

DMF: N,N-dimethylformamide
THF: tetrahydroftiran
DME: 1,2-dimethoxyethane

EXAMPLES

Intermediate Compound: 5-Chloro-3H-spiro[1-benzofuran-2,4'-piperidine]

Method A: This compound was prepared as described by Effland, R. C; Gardner, B. A; Strupczewski, J., *J. Heterocyclic Chem.*, 1981, 18, 811-814.

Method B:

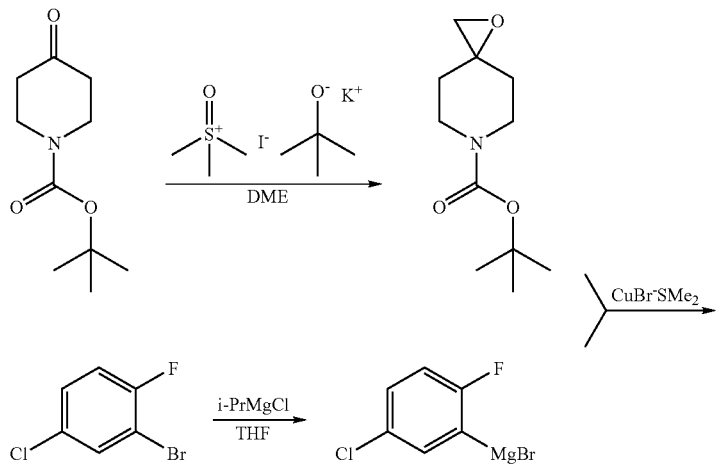

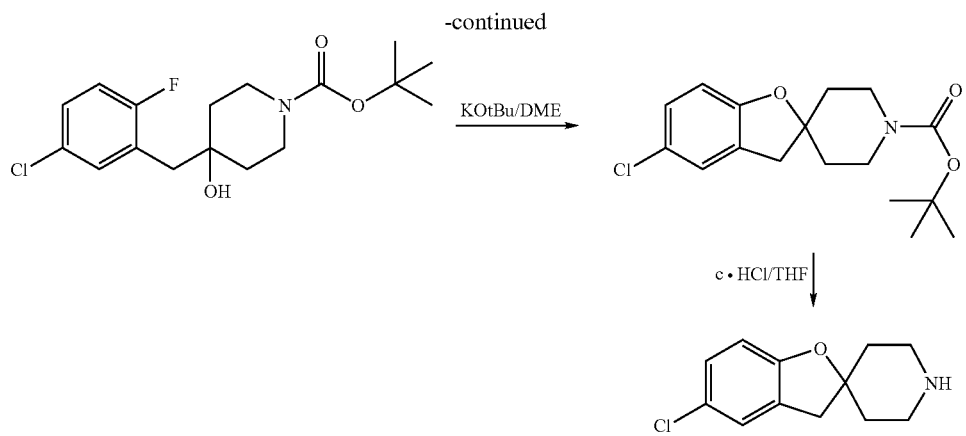

i) 1-Oxa-6-azaspiro[2.5]octane-6-carboxylic acid, 1,1-dimethylethyl ester

Potassium t-butoxide (31 g) was added to a stirred suspension of trimethylsulfoxonium iodide (60.8 g) in 1,2-dimethoxyethane (250 ml) at 20° C. After 1 hour, the mixture was added portionwise over 30 minutes to a stirred solution of 4-oxo-1-piperidinecarboxylic acid, 1,1-dimethylethyl ester (50 g) in 1,2-dimethoxyethane (50 ml) at 0° C. After a further 2 hours, water (500 ml) was added and the mixture extracted with tert.-butyl methyl ether (2×500 ml). The organic extracts were washed separately with saturated sodium bicarbonate solution (250 ml), combined, dried over anhydrous magnesium sulphate, filtered and evaporated under reduced pressure. The residual oil was co-evaoprated with toluene (100 ml) to give the sub-title compound (43.25 g, 81%) as a solid.

$^1$H-NMR (400 MHz, CDCl$_3$): δ 1.46 (9H, s), 1.43-1.48 (2H, m), 1.75-1.84 (2H, m), 2.69 (2H, s), 3.38-3.47 (2H, m), 3.70-3.75 (2H, m).

(ii) 5-Chlorospiro[1-benzofuran-2,4'-piperidine]-1'-carboxylic acid, 1,1-dimethyl ester A solution of iso-propylmagnesium chloride in tetrahydrofuran (2M, 106.6 ml) was added dropwise over 15 minutes to a stirred solution of 2-bromo-4-chloro-1-fluorobenzene (42.5 g) in anhydrous tetrahydrofuran (250 ml) at 0° C. under nitrogen. After a further 15 minutes, a solution of 1-oxa-6-azaspiro[2.5]octane-6-carboxylic acid, 1,1-dimethylethyl ester (43.2 g) in anhydrous tetrahydrofuran (50 ml) was added followed by copper(I)bromide dimethyl sulphide complex (0.4 g). The mixture was stirred at 40° C. for 18 hours, cooled to 20° C., diluted with water (300 ml) and extracted with tert.-butyl methyl ether (2×300 ml). Organic extracts were dried over anhydrous magnesium sulphate, filtered and evaporated under reduced pressure. The residual oil was dissolved in 1,2-dimethoxypropane (200 ml). Potassium tert-butoxide (22.8 g) was added and the mixture stirred at 40° C. for 16 hours then at 50° C. for 24 hours. Further potassium tert.-butoxide (5.7 g) was added and stirring continued at 50° C. for 2 hours then at 55° C. for 4 hours. Water (500 ml) was added and the mixture extracted with tert.-butyl methyl ether (2×300 ml). Organic extracts were dried over anhydrous magnesium sulphate, filtered and evaporated under reduced pressure to give the sub-title compound (47.45 g, 67%) as an oil.

$^1$H-NMR (400 MHz, CDCl$_3$): δ 1.47 (9 h, s), 1.67 (2H, td), 1.85-1.93 (2H, m), 2.94 (2H, s), 3.39 (2H, td), 3.65-3.80 (2H, m), 6.67 (1H, d), 7.06 (1H, d), 7.10 (1H, s).

iii) 5-Chlorospiro[1-benzofuran-2,4'-piperidine]

Concentrated hydrochloric acid (23 ml) was added to a solution of 5-chlorospiro[1-benzofuran-2,4'-piperidine]-1'-carboxylic acid, 1,1-dimethyl ester (46.43 g) in tetrahydrofuran (230 ml). The mixture was stirred at 50° C. for 6 hours, cooled to 20° C., diluted with water (230 ml) and extracted with tert.-butyl methyl ether (2×230 ml). The aqueous phase was adjusted to pH>10 by addition of 50 wt. % sodium hydroxide solution and extracted with tert.-butyl methyl ether (3×300 ml). Organic extracts were dried over anhydrous magnesium sulphate, filtered and evaporated under reduced pressure. The residual oil was dissolved in tetrahydrofuran (240 ml), concentrated hydrochloric acid (12 ml) was added and the mixture stirred at 20° C. for 16 hours. Precipitated solid was filtered and dissolved in water (100 ml). The solution was adjusted to pH>10 by addition of 50 wt. % sodium hydroxide solution and extracted with tert.-butyl methyl ether (3×100 ml) to give the title compound (13.3 g, 45%) as a solid.

$^1$H-NMR (400 MHz, CDCl$_3$): δ 1.69-1.76 (2H, m), 1.83-1.87 (2H, m), 2.78-2.84 (2H, m), 2.98-3.03 (4H, m), 6.65 (1H, d), 7.04 (1H, d), 7.13 (1H, s).

APCI-MS: m/z 224/6 [M+H]$^+$

Example 1

(2S)-1-(5-Chloro-1'H,3H-spiro[1-benzofuran-2,4'-piperidin]-1'-yl)-3-(2-methoxyphenoxy)propan-2-ol hydrochloride Step I:

(2S)-2-[(2-Methoxyphenoxy)]oxirane

A mixture of (2S)-oxiran-2-ylmethyl-3-nitrobenzenesulfonate (777 mg, 3.0 mmol), 2-methoxyphenol (372.5 mg, 3.0 mmol) and Cs$_2$CO$_3$ (1.3 g, 4.0 mmol) in DMF was stirred at room temperature overnight. The reaction mixture was partitioned between ethyl acetate and H$_2$O. The organic layer was dried over Na$_2$SO$_4$, filtered and concentrated. The residue was purified by silica gel flash chromatography (0-30% ethyl acetate in petroleum spirit 40-60) to give subtitled compound (425 mg).

¹H-NMR (CDCl₃, 400 MHz): δ 7.08-6.88 (m, 4H); 4.26 (dd, J=3.6, 11.4 Hz, 1H); 4.08 (dd, J=5.4, 11.4 Hz, 1H); 3.90 (s, 3H); 3.43 (m, 1H); 2.92 (t, J=4.8 Hz, 1H); 2.77 (dd, J=2.7, 5.0 Hz, 1H).

APCI-MS: m/z 222(MH⁺).

Step II:

(2S)-1-(5-Chloro-1'H,3H-spiro)[1-benzofuran-2,4'-piperidin]-1'-yl-3-(2-methoxyphenoxy)propan-2-ol A mixture of 5-chloro-3H-spiro[1-benzofuran-2,4'-piperidine] (150 mg, 0.67 mmol) and (2S)-2-[(2-methoxyphenoxy)methyl]oxirane (121 mg, 0.67 mmol) in ethanol (2 mL) was stirred at 80° C. overnight. The volatiles were removed in vacuo and the residue was purified by silica gel flash chromatography (0-1% methanol in dicholoromethane, 0.2% NH₄OH) to give the titled compound (190 mg).

¹H-NMR (CDCl₃, 400 MHz): δ 7.10 (m, 1H); 7.05 (dd, J=2.3, 8.5 Hz, 1H); 6.98-6.93 (m, 2H); 6.90 (m, 2H); 6.67 (d, J=8.5 Hz, 1H); 4.18 (m, 1H); 4.05 (d, J=5.0 Hz, 2H); 3.88 (s, 3H); 2.98 (s, 2H); 2.84 (m, 1H); 2.75 (m, 1H); 2.60 (m, 4H); 1.99 (m, 2H); 1.80 (m, 2H).

APCI-MS: m/z 403(MH⁺).

Example 2

2-{[(2S)-3-(5-Chloro-1'H,3H-spiro[1-benzofuran-2,4'-piperidin]-1'-yl)-2-hydroxypropyl]oxy}phenol To a solution of (2S)-1-(5-chloro-1'H,3H-spiro[1-benzofuran-2,4'-piperidin]-1'-yl)-3-(2-methoxyphenoxy)propan-2-ol (180 mg, 0.444 mmol) in dicholoromethane (4 mL) was added 1M BBr₃ solution in CH₂Cl₂ (1.32 mL, 1.32 mmol) at 0° C. After the addition was completed, the reaction mixture was stirred at 0° C. for 1.5 h. Methanol (1 mL) was added and the reaction mixture was stirred at 0° C. for 10 min, and concentrated in vacuo. The residue was dissolved in ethyl acetate and washed succesively with aqueous NaHCO₃ and H₂O. The organic layer was dried over Na₂SO₄, filtered and concentrated. The residue was purified by silica gel flash chromatography (0-1.5% methanol in dichloromethane, 0.2% NH₄OH) to give the titled compound (150 mg).

¹H-NMR (CD₃OD, 400 MHz): δ 7.14 (m, 1H); 7.04 (dd, J=2.4, 8.5 Hz, 1H); 6.94 (m, 1H); 6.85-6.74 (m, 3H); 6.65 (d, J=8.5 Hz, 1H); 4.18 (m, 1H); 4.04 (dd, J=4.0, 9.9 Hz, 1H); 3.95 (dd, J=5.9, 9.9 Hz, 1H); 3.04 (s, 2H); 2.79-2.57(m, 6H); 2.00-1.82(m, 4H).

APCI-MS: m/z 390(MH⁺).

Example 3

(2S)-1-(5-Chloro-1'H,3H-spiro[1-benzofuran-2,4'-piperidin]-1'-yl)-3-[2-(2-hydroxyethoxy)phenoxy]propan-2-ol hydrochloride A mixture of 2-{[(2S)-3-(5-Chloro-1'H,3H-spiro[1-benzofuran-2,4'-piperidin]-1'-yl)-2-hydroxypropyl]oxy}phenol (50 mg, 0.128 mmol), chloroethanol (103 mg, 1.28 mmol) and K₂CO₃ (207 mg, 1.5 mmol) in DMF (1.5 mL) was stirred at 83° C. for 4 h. The reaction mixture was cooled to room temperature and partitioned between ethyl acetate and H₂O. The organic layer was dried over Na₂SO₄, filtered and concentrated in vacuo. The residue was purified by silica gel flash chromatography (0-2.5% methanol in dichloromethane, 0.2% NH₄OH) to give the titled compound (40 mg).

¹H-NMR (CD₃OD, 400 MHz): δ 7.13 (m, 1H); 7.06-6.97 (m, 3H); 6.94-6.90 (m, 2H); 6.65 (d, J=8.5 Hz, 1H); 4.17 (m, 1H); 4.10-4.03 (m, 3H); 3.96 (dd, J=6.2, 9.9 Hz, 1H); 3.89-3.85 (m, 2H); 3.02 (s, 2H); 2.76-2.56 (m, 6H); 1.98-1.78 (m, 4H).

APCI-MS: m/z 434(MH⁺).

Example 4

2-(2-{[(2S)-3-(5-Chloro-1'H,3H-spiro[1-benzofuran-2,4'-piperidin]-1'-yl)-2-hydroxypropyl]oxy}phenyl)-N-methylacetamide trifluoroacetate (salt)

Step 1:

N-Methyl-2-{2-[(2S)-oxiran-2-ylmethoxy]phenyl}acetamide

A mixture of 2-(2-hydroxyphenyl)-N-methylacetamide (1.00 g, 6.1 mmol) prepared according to a known procedure (Bernd, Peschke, *Eur. J. Med. Chem.*, 2000, 35, 599-618), (2S)-oxiran-2-ylmethyl 3-nitrobenzenesulfonate (1.58 g, 6.1 mmol) and cesium carbonate (2.37 g, 7.3 mmol) in 1-methylpyrrolidin-2-one (15 ml) was stirred at room temperature overnight. The mixture was diluted with water and extracted with ethyl acetate, the combined organic layers were dried with sodium sulphate, volatiles were removed in vacuo. The residue was purified by recrystillaziation from ethyl acetate/heptane; (390 mg) of the subtitle compound was obtained.

¹H-NMR (CDCl₃, 400 MHz): δ 7.30-7.23 (m, 2H); 7.00-6.96 (m, 1H); 6.89 (d, J=8.3 Hz, 1H); 5.97 (br. s, 1H); 4.37 (dd, J=2.6, 11.1 Hz, 1H); 4.05-3.99 (m, 1H); 3.58 (br. s, 2H); 3.41-3.36 (m, 1H); 2.94 (t, J=4.4 Hz, 1H); 2.86-2.83 (m, 1H); 2.75 (d, J=4.9 Hz, 3H).

APCI-MS: m/z 222 (MH⁺)

Step II:

2-(2-{[(2S)-3-(5-Chloro-1'H,3H-spiro[1-benzofuran-2,4'-piperidin]-1'-yl)-2-hydroxypropyl]oxy}phenyl)-N-methylacetamide trifluoroacetate A mixture of N-methyl-2-{2-[(2S)-oxiran-2-ylmethoxy]phenyl}acetamide (23 mg, 0.1 mmol) and 5-chloro-3H-spiro[1-benzofuran-2,4'-piperidine] (22 mg, 0.1 mmol) in ethanol (15 mL) was heated at reflux overnight, volatiles were removed in vacuo. The residue was purified by HPLC (acetonitrile/water, 0.1% trifluoroacetic acid) and gave (25 mg) of the subtitle compound.

¹H-NMR (CDCl₃, 400 MHz): δ 7.63-7.52 (m, 3); 7.44 (dd, J=2.1, 8.5 Hz, 1H); 7.37-7.28 (m, 2H); 7.08 (d, J=8.5 Hz, 1H); 4.82-4.72 (m, 1H); 4.46-4.35 (m, 2H); 4.10-3.96 (m, 2H); 3.96-3.69 (m, 6H); 3.47 (br. s, 2H); 3.05 (s, 3H); 2.63-2.45 (m, 4H).

APCI-MS: m/z 445 (MH⁺)

Example 5

(3S)-1-[(2-{[(2S)-3-(5-Chloro-1'H,3H-spiro[1-benzofuran-2,4'-piperidin]-1'-yl)-2-hydroxypropyl]oxy}phenyl)acetyl]pyrrolidin-3-ol Step I:

(3S)-1-[(2-Hydroxyphenyl)acetyl]pyrrolidin-3-ol

A mixture of (2-hydroxyphenyl)acetic acid (304 mg, 2.0 mmol) and N,N'-carbonyldiimidazole (405 mg, 2.5 mmol) in DMF (5 nL) was stirred at room temperature for 45 min. A solution of (3S)-pyrrolidin-3-ol (435 mg, 5.0 mmol) in DMF (1.5 mL) was added and the reaction mixture was stirred at room temperature overnight. The reaction mixture was partitioned between ethyl acetate and H₂O. The organic layer was dried over Na₂SO₄, filtered and concentrated. The residue was purified by silica gel flash chromatography (0-3% methanol in dichloromethane) to give the subtitled compound (205 mg).

¹H-NMR (CD₃OD, 400 MHz): δ 7.68 (s, 1H); 7.13-7.03 (m, 3H); 6.77 (m, 1H); 4.40 (m, 1H); 3.80-3.45 (m, 6H); 2.10-1.84 (m, 2H).

APCI-MS: m/z 222 (MH⁺).

Step II:

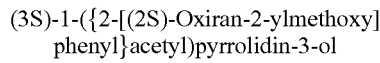

(3S)-1-({2-[(2S)-Oxiran-2-ylmethoxy]phenyl}acetyl)pyrrolidin-3-ol

A mixture of (2S)-oxiran-2-ylmethyl-3-nitrobenzenesulfonate (228 mg, 0.88 mmol), (3S)-1-[(2-hydroxyphenyl)acetyl]pyrrolidin-3-ol (196 mg, 0.88 mmol) and Cs₂CO₃ (344 mg, 1.05 mmol) in DMF (5 mL) was stirred at room temperature overnight. The reaction mixture was partitioned between ethyl acetate and H₂O. The organic layer was dried over Na₂SO₄, filtered and concentrated. The residue was purified by silica gel flash chromatography/(0-3% methanol in dichloromethane) to give the subtitled compound (35 mg).

¹H-NMR (CD₃OD, 400 MHz): δ 7.26-7.15 (m, 2H); 6.97-6.88 (m, 2H); 4.48-4.30 (m, 2H); 3.94-3.45 (m, 8H); 2.86 (t, J=4.8 Hz, IfH); 2.73 (m, 1H); 2.16-1.86 (m, 2H).

APCI-MS: m/z 278(MH⁺).

Step III:

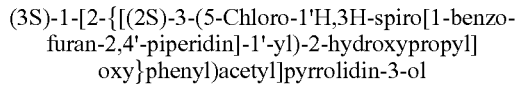

(3S)-1-[2-{[(2S)-3-(5-Chloro-1'H,3H-spiro[1-benzofuran-2,4'-piperidin]-1'-yl)-2-hydroxypropyl]oxy}phenyl)acetyl]pyrrolidin-3-ol A mixture of 5-chloro-3H-spiro[1-benzofuran-2,4'-piperidine] (26 mg, 0.115 mmol) and (3S)-1-({2-[(2S)-oxiran-2-ylmethoxy]phenyl}acetyl)pyrrolidin-3-ol (32 mg, 0.115 mmol) in ethanol (2 mL) was stirred at 80° C. overnight. The volatiles were removed in vacuo and the residue was purified by silica gel flash chromatography (0-2% methanol in dichloromethane, 0.2% NH₄OH) to give the titled compound (33 mg).

¹H-NMR (CD₃OD, 400 MHz): δ 7.24 (m, 1H); 7.19 (d, J=7.3 Hz, 1H); 7.14 (s, 1H); 7.05 (dd, J=2.0, 8.5 Hz, 1 if); 6.97 (d, J=8.2 Hz, 1H); 6.91 (t, J=7.3 Hz, 1H); 6.65 (d, J=8.5 Hz, 1H); 4.46 (m, 0.5H); 4.42 (m, 0.5H); 4.15 (m, 1 if); 4.05 (m, 1H); 3.97 (dd, J=5.9, 9.8 Hz, 1H); 3.75-3.47 (m, 6H); 3.00 (s, 2H); 2.74-2.52 (m, 6H); 2.14-1.80 (m, 6H).

APCI-MS: m/z 501 (MH⁺).

Example 6

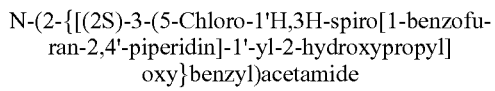

N-(2-{[(2S)-3-(5-Chloro-1'H,3H-spiro[1-benzofuran-2,4'-piperidin]-1'-yl-2-hydroxypropyl]oxy}benzyl)acetamide Step I:

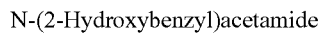

N-(2-Hydroxybenzyl)acetamide

2-Methoxybenzylamine (822 mg, 6.0 mmol) in methanol (10 mL) was treated with acetic anhydride (613 mg, 6.0 mmol) at room temperature for 2 h. The volatiles were removed in vacuo. The residue was dissolved in CH₂Cl₂, cooled to 0° C., 1M solution of BBr₃ in CH₂Cl₂ (12 mL, 12.0 mml) was added slowly. After addition was completed the reaction mixture was stirred at room temperature overnight, cooled to 0° C., methanol (3 mL) was added and after 10 min volatiles were removed in vacuo. The residue was dissolved in ethyl acetate, washed successively with aqueous NaHCO₃ and H₂O. The organic layer was dried over Na₂SO₄ filtered and concentrated. The residue was purified by silica gel flash chromatography (0-50% ethyl acetate in petroleum spirit) to give the subtitled compound (400 mg).

¹H-NMR (CD₃OD, 400 MHz): δ 7.16-7.06 (m, 2H); 6.81-6.74 (m, 2H); 4.18 (s, 2H); 1.99 (s, 3H).

APCI-MS: m/z 166 (MH⁺).

Step II:

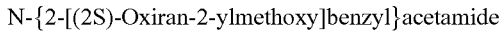

N-{2-[(2S)-Oxiran-2-ylmethoxy]benzyl}acetamide

A mixture of N-(2-hydroxybenzyl)acetamide (382 mg, 2.31 mmol), (2S)-oxiran-2-ylmethyl-3-nitrobenzenesulfonate (599 mg, 2.31 mmol) and Cs₂CO₃ (901 mg, 2.77 mmol) in DMP (5 mL) was stirred at room temperature overnight. The reaction mixture was partitioned between ethyl acetate and H₂O. The organic layer was dried over Na₂SO₄, filtered and concentrated. The residue was purified by silica gel flash chromatography (0-80% ethyl acetate in petroleum spirit) to give the subtitled compound (333 mg).

¹H-NMR (CDCl₃, 400 MHz): δ 7.32-7.22 (m, 2H); 6.95 (m, 1H); 6.87 (m, 1H); 6.34 (br.s, 1H); 4.55-4.354 (m, 3H); 4.03 (dd, J=5.1, 11.2 Hz, 1H); 3.39 (m, 1H); 2.95 (m, 1H); 2.86 (m, 1H); 1.98 (s, 3H).

APCI-MS: m/z 222(MH⁺).

Step III:

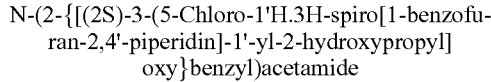

N-(2-{[(2S)-3-(5-Chloro-1'H.3H-spiro[1-benzofuran-2,4'-piperidin]-1'-yl-2-hydroxypropyl]oxy}benzyl)acetamide A mixture of 5-chloro-3H-spiro[1-benzofuran-2,4'-piperidin] (64 mg, 0.284 mmol) and N-{2-[(2S)-oxiran-2-ylmethoxy]benzyl}acetamide (63 mg, 0.284 mmol) in ethanol (1.5 mL) was stirred at 80° C. overnight. The volatiles were removed in vacuo and the residue was purified by silica gel flash chromatography (0-1% methanol in dichloromethane, 0.2% NH₄OH) to give the titled compound (85 mg).

¹H-NMR (CD₃OD, 400 MHz): δ 7.28-7.21 (m, 2H); 7.14 (s, 1H); 7.04 (dd, J=2.2, 8.4 Hz, 1H); 6.97 (d, J=8.1 Hz, 1H); 6.91 (t, J=7.4 Hz, 1H); 6.65 (d, J=8.5 Hz, 1H); 4.39 (s, 2H); 4.18 (m, 1H); 4.09 (dd, J=3.9, 9.8 Hz, 1H); 3.98 (dd, J=5.9, 9.8 Hz, 1H); 3.02 (s, 2H); 2.79-2.58 (m, 6H); 1.99-1.80 (m, 7H).

APCI-MS: m/z 445 (MH⁺).

Example 7

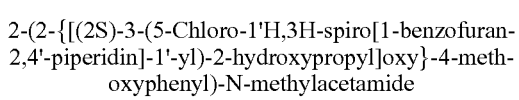

2-(2-{[(2S)-3-(5-Chloro-1'H,3H-spiro[1-benzofuran-2,4'-piperidin]-1'-yl)-2-hydroxypropyl]oxy}-4-methoxyphenyl)-N-methylacetamide Step I

2-(2,4-Dimethoxyphenyl)-N-methylacetamide

A mixture of (2,4-dimethoxyphenyl)acetic acid (577 mg, 3.0 mmol) and N,N-carbonyldiimidazole (608 mg, 3.75 mmol) in DMF (10 mL) was stirred at room temperature for 45 min, aqueous 40% methyl amine (4.5 mL) was added and the reaction mixture was stirred at room temperature over the week-end. The reaction mixture was is partitoned between ethyl acetate and H₂O. The organic layer was dried over Na₂SO₄, filtered and concentrated. The residue was purified by silica gel flash chromatography (0-80% ethyl acetate in petroleum spirit) to give the subtitled compound (460 mg).

¹H-NMR (CDCl₃, 400 MFz): δ 7.12 (d, J=7.8 Hz, 1H); 6.48 (m, 2H); 5.64 (br.s, 1H); 3.83 (s, 3H); 3.81 (s, 3H); 3.25 (s, 2H); 2.73 (d, J=4.8 Hz, 3H).

APCI-MS: m/z 210 (MH⁺).

Step II:

2-(2-Hydroxy-4-methoxyphenyl)-N-methylacetamide

To a solution of 2-(2,4-dimethoxyphenyl)-N-methylacetamide (445 mg, 2.12 mmol) in CH₂Cl₂ (10 mL) was slowly added 1M BBr₃ solution in CH₂Cl₂ (6.4 mL, 6.4 mmol). After addition was completed, the reaction mixture was stirred at 0° C. for 2.5 h, methanol (2 mL) was added and after 15 min the volatiles were removed in vacuo. The residue was dissolved in ethyl acetate, washed successively with aqueous NaHCO₃ and H₂O. The organic layer was dried over Na₂SO₄, filtered and concentrated. The residue was purified by silica gel flash chromatography (0-5% methanol in dichloromethane) to give the subtitled compound (16 mg) along with 2-(4-hydroxy-2-methoxyphenyl)-N-methylacetamide (30 mg).

2-(2-Hydroxy-4-methoxyphenyl)-N-methylacetamide

¹H-NMR (CDCl₃, 400 MHz): δ 6.87 (d, J=8.2 Hz, 1H); 6.56 (d, J=2.6 Hz, 1H); 6.38 (dd, J=2.7, 8.4 Hz, 1H); 6.08 (br.s, 1H); 3.78 (s, 3H); 3.49 (s, 2H); 2.83 (d, J=4.8 Hz, 3H).

APCI-MS: m/z 182 (MH⁺).

2-(4-Hydroxy-2-methoxyphenyl)-N-methylacetamide

¹H-NMR (CDCl₃, 400 MHz): δ 6.97 (d, J=8.2 Hz, 1H), 6.50 (d, J=2.4 Hz, 1H), 6.44 (dd, J=8.2, 2.4 Hz, 1H), 5.92 (d, J=4.4 Hz, 1H), 3.76 (s, 3H), 3.48 (s, 2H), 2.76 (d, J=4.8 Hz, 3H).

APCI-MS: m/z 182 (MH⁺).

Step III:

2-{4-Methoxy-2-[(2S)-oxiran-2-ylmethoxy]phenyl}-N-methylacetamide

A mixture of 2-(2-hydroxy-4-methoxyphenyl)-N-methylacetamide (15 mg, 0.076 mmol), (2S)-oxiran-2-ylmethyl 3-nitrobenzenesulfonate (20 mg, 0.076 mmol) and Cs₂CO₃ (30 mg, 0.091 mmol) in DMF (1.5 mL) was stirred at room temperature overnight. The reaction mixture was partitioned between ethyl acetate and H₂O. The organic layer was dried over Na₂SO₄, filtered and concentrated. The residue was purified by silica gel flash chromatography (0-100% ethyl acetate in petroleum spirit) to give the subtitled compound (18 mg).

¹H-NMR (CDCl₃, 400 MHz): δ 7.17 (d, J=8.2 Hz, 1H); 6.52-6.46 (m, 2H); 5.90 (br.s, 1H); 4.33 (dd, J=2.6, 11.1 Hz, 1H); 3.97 (dd, J=5.2, 11.1 Hz, 1H); 3.80 (s, 3H); 3.49 (s, 2H); 3.36 (m, 1H); 2.93 (t, J=4.7 Hz, 1H); 2.82 (dd, J=2.6, 4.7 Hz, 1H); 2.74 (d, J=4.9 Hz, 3H).

APCI-MS: m/z 252 (MH⁺).

Step IV:

2-(2-{[(2S)-3-(5-Chloro-1'H,3H-spiro[1-benzofuran-2,4'-piperidin]-1'-yl)-2-hydroxypropyl]oxy}-4-methoxyphenyl)-N-methylacetamide A mixture of 5-chloro-3H-spiro[1-benzofuran-2,4'-piperidin] (16 mg, 0.0716 mmol) and 2-{4-methoxy-2-[(2S)-oxiran-2-ylmethoxy]phenyl}-N-methylacetamide (18 mg, 0.0716 mmol) in ethanol (1 mL) was stirred at 80° C. overnight. The volatiles were removed in vacuo and the residue was purified by silica gel flash chromatography (0-1% methanol in dichloromethane, 0.2% NH₄OH) to give the titled compound (16 mg).

¹H-NMR (CD₃OD, 400 MHz): δ 7.23 (s, 1H); 7.20 (d, J=8.3 Hz, 1H); 7.14 (dd, J=2.2, 8.5 Hz, 1H); 6.73 (d, J=8.5 Hz, 1H); 6.65 (d, J=2.4 Hz, 1H); 6.59 (dd, J=2.4, 8.3 Hz, 1H); 4.25 (m, 1H); 4.14 (dd, J=3.9, 9.7 Hz, 1H); 4.05 (dd, J=5.7, 9.7 Hz, 1H); 3.88 (s, 3H); 3.55 (s, 2H); 3.11 (s, 2H); 2.86-2.64 (m, 9H); 2.03 (m, 2H); 1.94 (m, 2H).

APCI-MS: m/z 475 (MH⁺).

Example 8

2-(2-{[(2S)-3-(5-Chloro-1'H,3H-spiro[1-benzofuran-2,4'-piperidin]-1'-yl)-2-hydroxypropyl]oxy}-4-hydroxyphenyl)-N-methylacetamide trifluoroacetate (salt)

To a solution of 2-(2-{[(2S)-3-(5-chloro-1'H,3H-spiro[1-benzofuran-2,4'-piperidin]-1'-yl)-2-hydroxypropyl]oxy}-4-methoxyphenyl)-N-methylacetamide (12 mg, 0.025 mmol) in CH₂Cl₂ (1 mL) was slowly added 1M BBr₃ solution in CH₂Cl₂ ((0.075 mL) at 0° C. After addition was completed the reaction mixture was stirred at 0° C. for 80 min, 0.3 mL methanol was added and after 10 min the volatiles were removed in vacuoand the residue was subjected to HPLC (10-55% CH₃CN in H2O, 0.1% CF₃CO₂H) to give the titled compound (7 mg).

¹H-NMR (CD₃OD, 400 MFz): δ 7.20 (s, 1H); 7.10 (m, 1H); 7.01 (d, J=8.1 Hz, 1H); 6.74 (m, 1H); 6.43 (s, 1H); 6.39 (dd, J=2.0, 8.1 Hz, 1H); 4.40 (m, 1H); 4.00 (m, 2H); 3.69 (m, 2H); 3.53-3.34 (m, 6H); 3.13 (s, 2H); 2.69 (s, 3H); 2.29-2.06 (m, 4H).

APCI-MS: m/z 461 (MH⁺).

Example 9

2-(4-{[(2S)-3-(5-Chloro-1'H,3H-spiro[1-benzofuran-2,4'-piperidin]-1'-yl)-2-hydroxypropyl]oxy}-2-methoxyphenyl)-N-methylacetamide Step I:

2-{2-Methoxy-4-[(2S)-oxiran-2-ylmethoxy]-N-methylacetamide

A mixture of (2S)-oxiran-2-ylmethyl 3-nitrobenzenesulfonate (37 mg, 0.143 mmol), 2-(4-hydroxy-2-methoxyphenyl)-N-methylacetamide (28 mg, 0.143 mmol) and cesium carbonate (58 mg, 0.178 mmol) in DMF (2 mL) was stirred at room temperature over night. The reaction mixture was partitioned between ethyl acetate and H₂O. The organic layer was dried over Na₂SO₄, filtered and concentrated in vacuo. The residue was purified by silica gel flash chromatography (0-1% methanol in CH₂Cl₂) to give the subtitled compound (21 mg).

¹H-NMR (CDCl₃, 400 MHz): δ 7.12 (d, J=8.3 Hz, 1H); 6.55 (d, J=2.3 Hz, 1H); 6.48 (dd, J=2.3, 8.0 Hz, 1H); 5.58 (brs, 1H); 4.26 (dd, J=2.9, 11 Hz, 1H); 3.95 (dd, J=5.8, 11.0 Hz, 1H); 3.82 (s, 3H); 3.42 (s, 2H); 3.36 (m, 1H); 2.93 (t, J=4.7 Hz, 1H); 2.77 (dd, J=2.6, 4.9 Hz, 1H); 2.74 (d, J=4.9 Hz, 3H).
APCI-MS: m/z 252(MH⁺).

Step II:

2-(4-{[(2S)-3-(5-Chloro-1'H,3H-spiro[1-benzofuran-2,4'-piperidin]-1'-yl)-2-hydroxypropyl]oxy}-2-methoxyphenyl)-N-methylacetamide A mixtre of 5-chloro-3H-spiro[1-benzofuran-2,4'-piperidine] (16 mg, 0.071 mmol) and 2-{2-methoxy-4[(2S)-oxiran-2-ylmethoxy]-N-methylacetamide (18 mg, 0.071 mmol) in ethanol (2 mL) was stirred at 80° C. over night. The volatiles were removed in vacuo and the residue was purified by silica gel flash chromatography (0-1% methanol in CH₂Cl₂, 0.2% NH₄OH) to give the titled compound (20 mg).
¹H-NMR (CD₃OD, 400 MHz): δ 7.7.13 8 s, 1H); 7.07 (d, J=8.3 Hz, 1H); 7.04 (dd, J=1.9, 8.5 Hz, 1H); 6.65 (d, J=8.5 Hz, 1H); 6.58 (d, J=2.2 Hz, 1H); 6.51 (dd, J=2.2, 8.3 Hz, 1H); 4.16-4.09 (m, 1H); 4.01 (dd, J=4.1, 9.7 Hz, 1H); 3.93 (dd, J=5.8, 9.7 Hz, 1H); 3.80 (s, 3H); 3.40 (s, 2H); 3.00 (s, 2H); 2.78-2.52 (m, 9H); 1.98-1.78 (m, 4H).
APCI-MS: m/z 475(MH⁺).

Example 10

(2S)-1-(2-Amino-5-methoxyphenoxy)-3-(5-chloro-1'H,3H-spiro[1-benzofuran-2,4'-piperidin]-1'-yl)propan-2-ol bis(trifluoroacetate) (salt)

Step I:

N-(2-Hydroxy-4 methoxyphenyl)acetamide

2-Nitro-5-methoxyphenol (prepared from 3-methoxyphenol, R. J. Maleski, *Synthetic Communications*, 1993, 23, 343-348) (48.5 g, 0.287 mol) dissolved in THF (1.5 L) was hydrogenated at ambient temperature over night with 10% palladium on carbon (10 g) until 20.3 L of hydrogen was consumed. After filtration and evaporation the residue was suspended in degassed water (1.7 L) and acetic anhydride (42.5 mL) was added with stirring. The mixture was heated to 60° C. for 1 h and then cooled to room temperature. The volatiles were removed in vacuo and the solid was washed thoroughly with water and dried in vacuo to give brick-red crystals (41.7 g, 80%).
¹H-NMR (400 MHz, CDCl₃): δ 8.98 (s, 1H); 7.34 (br.s, 1H); 6.81 (d, 1H); 6.58 (d, 1H); 6.44 (dd, 1H); 3.78(s, 3H); 2.26(s, 3H)

Step II:

N-{4-Methoxy-2[(2S)-oxiran-2-ylmethoxy]phenyl}acetamide

N-(2-Hydroxy-4-methoxyphenyl)acetamide (18.12 g, 0.1 mol) and (2S)-oxiran-2-ylmethyl 3-nitrobenzenesulfonate (25.92 g, 0.1 mol) were dissolved in dry DMF (75 mL) and stirred under nitrogen (N₂) on an ice-bath. Cesium carbonate (35.8 g, 0.11 mol) was added and the stirring under N₂ was continued at ambient temperature overnight. The mixture was poured into ethyl acetate (1 L) and water (250 mL). The organic phase was washed with water (3×250 mL), dried over Na₂SO₄, filtered and concentrated in vacuo to give an orange solid crude product (29 g), which was recrystallized from ethanol (100 mL) and washed with ether to give white crystals. More white crystals were obtained from the mother liquor, after evaporation and recrystillazition from 2-propanol. Total yield 15 g (63%).
¹H-NMR (CDCl₃): δ 8.22 (d, 1H); 7.64 (bs, 1H); 6.53 (dd, 1H); 6.50 (d, 1H); 4.34 (dd, 1H); 3.92 (dd, if); 3.79 (s, 3H); 3.38 (m, if); 2.96 (t, 1H); 2.78 (dd, 1H); 2.20 (s, 3H)

Step III:

N-(2-{[(2S)-3-(5-Chloro-1'H,3H-spiro[1-benzofuran-2,4'-piperidin]-1'-yl)-2-hydroxypropyl]oxy}methoxyphenyl)acetamide A mixture of 5-chloro-3H-spiro[1-benzofuran-2,4'-piperidine] (200 mg, 0.894 mmol) and N-{4-methoxy-2[(2S)-oxiran-2-ylmethoxy]phenyl}acetamide (212 mg, 0.894 mmol) in ethanol (5 mL) was stirred at 80° C. overnight. The volatiles were removed in vacuo and the residue was purified by silica gel flash chromatography (0-2% methanol in dichloromethane, 0.2% NH₄OH) to give the titled compound (400 mg).
¹H-NMR (CD₃OD, 400 MHz): δ 7.74 (d, J=8.9 Hz, 1H); 7.13 (m, 1H); 7.04 (dd, J=2.3, 8.5 Hz, 1H); 6.65 (d, J=8.5 Hz, 1H); 6.61 (d, J=2.7 Hz, 1H); 6.51 (dd, J=2.7, 8.8 Hz, 1H); 4.17 (m, 1H); 4.08 (dd, J=3.4, 10.0 Hz, 1H); 3.98 (dd, J=6.3, 9.9 Hz, 1 if); 3.79 (s, 3H); 3.03 (s, 2H); 2.72(m, 4H); 2.62 (m, 2H); 2.15(s, 3H); 1.95 (m, 2H); 1.84 (m, 2H).
APCI-MS: m/z 461 (MH⁺).

Step IV:

(2S)-1-(2-Amino-5-methoxyphenoxy)-3-(5-chloro-1'H,3H-spiro[1-benzofuran-2,4'-piperidin]-1'-yl)propan-2-ol bis(trifluoroacetate) (salt)

A solution of N-(2-{[(2S)-3-(5-Chloro-1'H,3H-spiro[1-benzofuran-2,4'-piperidin]-1'-yl)-2-hydroxypropyl]oxy}-4-methoxyphenyl)acetamide (0.23 g, 0.5 mmol) in 1M aq. HCl (10 ml) was heated with reflux for 5 h. The reaction mixture was then concentrated in vacuo, and purified by HPLC to afford colourless solid (0.175 g, 54%).
¹H-NMR (400, d₆-DMSO): δ 7.28 (s, 1H), 7.15 (dd, J=8.5, 2.3 Hz, 2H), 7.07 (br.s, 1H), 6.78 (d, J=8.5 Hz, 1H), 6.67 (s, 1H), 6.53 (d, J=8.6 Hz, 1H), 6.09 (s, 1H), 4.33 (m, 1H), 4.02 (m, 2H), 3.72 (s, 3H), 3.66-3.22 (m, 6H), 3.11 (s, 2H), 2.22-1.95 (m, 4H).
APCI-MS: m/z 419 (MH⁺).

Example 11

N-(2-{[(2S)-3-(5-Chloro-1'H,3H-spiro[1-benzofuran-2,4'-piperidin]-1'-yl)-2-hydroxypropyl]oxy}-4-hydroxyphenyl)methanesulfonamide trifluoroacetate (salt)

Step I

N-(2-{[(2S)-3-(5-Chloro-1'H,3H-spiro[1-benzofuran-2,4'-piperidin]-1'-yl)-2-hydroxypropy]oxy}-4-hydroxyphenyl)acetamide To a cold (0° C.) solution of N-(2-{[(2S)-3-(5-chloro-1'H,3H-spiro[1-benzofuran-2,4'-piperidin]-1'-yl)-2-hydroxypropyl]oxy}4-methoxyphenyl)acetamide (see Ex. 10) (380 mg, 0.82 mmol) in dichloromethane (8 mL) was added 1M solution of boron tribromide (BBr₃) in dichloromethane (2.47 mL, 2.47 mmol) slowly. After addition was complete the icebath was removed and the reaction mixture was stirred at room temperature for 2 h 30 min. The reaction mixture was cooled to 0° C. and methanol (2 mL) was added slowly with stirring for 10 min. The volatiles were removed in vacuo. The residue was dissolved in large volume of ethyl acetate, washed successively with aqueous sodium hydrogencarbonate (NaHCO$_3$) solution and water. The organic layer was dried over Na$_2$SO4, filtered, concentrated and the residue was purified by silica gel flash chromatography (0-3% methanol in dichloromethane, 0.2% NH$_4$OH) to give the titled compound (155 mg).

$^1$H-NMR (CD$_3$OD, 400 MH): δ 7.57 (d, J=8.7 Hz, 1H); 7.14 (m, 1H); 7.04 (dd, J=2.3, 8.5 Hz, 1H); 6.66 (d, J=8.5 Hz, 1H); 6.48 (d, J=2.5 Hz, 1H); 6.32 (dd, J=2.5, 8.6 Hz, 1H); 4.17 (m, 1H); 4.06 (dd, J=3.4, 9.8 Hz, 1H); 3.93 (dd, J=6.2, 9.8 Hz, 1H); 3.03 (s, 2H); 2.70 (m, 4H); 2.59 (m, 2H); 2.13 (s, 3H); 1.95 (m, 2H); 1.84 (m, 2H).

APCI-MS: m/z 447 (MH$^+$).

Step II:

4-Amino-3-{[(2S)-3-(5-chloro-1'H,3H-spiro[1-benzofuran-2,4'-piperidin]-1'-yl)-2-hydroxypropyl]oxy}phenol bis(trifluoroacetate) (salt)

N-(2-{[(2S)-3-(5-Chloro-1'H,3H-spiro[1-benzofuran-2,4'-piperidin]-1'-yl)-2-hydroxypropyl]oxy}4-hydroxyphenyl)acetamide (135 mg, 0.3 mmol) was stirred in 1M hydrochloric acid (3 mL) at 100° C. for 2 h. The reaction mixture was concentrated in vacuo. After purification by preparative HPLC the subtitled compound was obtained as a white amorphous solid (150 mg).

$^1$H-NMR (MeOH-d$_4$, 400 MHz): δ 7.21 (bs, 1H); 7.18 (d, J=8.8 Hz, 1H); 7.11 (dd, J=2.0, 8.4 Hz, 1H); 6.74 (d, J=8.4 Hz, 1H); 6.62 (d, J=2.4 Hz, 1H); 6.49 (dd, J=2.4, 8.8 Hz, 1H); 4.58-4.49 (m, 1H); 4.13 (d, J=4.8 Hz, 2H); 3.8-3.6 (m, 2H); 3.6-3.4 (m, 2H); 3.48 (d, J=13.2 Hz, 1H); 3.45 (d, J=13.2 Hz, 1H); 3.16 (s, 2H); 2.31-2.17 (m, 4H)

APCI-MS: m/z 405 (MH$^+$)

Step III:

To a stirred solution of 4-Amino-3-{[(2S)-3-(5-chloro-1'H,3H-spiro[1-benzofuran-2,4'-piperidin]-1'-yl)-2-hydroxypropyl]-oxy}phenol bis(trifluoroacetate) (43 mg, 0.11 mmol) in dichloromethane (10 ml) was added pyridine (100 μl). The mixture was cooled to 0° C., and methanesulfonyl chloride was added (12 mg, 0.11 mmol). The reaction mixture was stirred at room temperature for 1 hour, then concentrated in vacuo, and purified by semi-preparative HPLC to afford colourless solid (24 mg, 37%).

$^1$H-NMR (400 MHz, d$_6$-DMSO): δ 9.63 (s, 1H), 9.53 (br.s, 1H), 8.53 (s, 1H), 7.30 (s, 1H), 7.16 (dd, J=8.5, 1.8 Hz, 1H), 7.05 (d, J=8.5 Hz, 1H), 6.79 (d, J=8.5 Hz, 1H), 6.44 (d, J=2.1 Hz, 1H), 6.37 (dd, J=8.5, 2.4 Hz, 1H), 6.00 (br.s, 1H), 4.34 (br.s, 1H), 3.89 (m, 2H), 3.64-3.15 (m, 8H), 3.11 (s, 1H), 2.86 (s, 3H), 2.23-2.00 (m, 4H)

APCI-MS: m/z 483 (MH$^+$).

Example 12

N-(2-{[(2S)-3-(5-Chloro-1'H,3H-spiro[1-benzofuran-2,4'-piperidin]-1-yl)-2-hydroxypropyl]oxy}-4-methoxyphenyl)methanesulfonamide trifluoroacetate (salt)

To a stirred solution of (25)-1-(2-amino-5-methoxyphenoxy)-3-(5-chloro-1'H,3H-spiro[1-benzofuran-2,4'-piperidin]-1'-yl)propan-2-o bis(trifluoroacetate) (65 mg, 0.1 mmol) in dichloromethane (10 ml) was added pyridine (50 μl). The mixture was cooled to 0° C., and methanesulfonyl chloride was added (11.4 mg, 0.1 mmol). The reaction mixture was stirred at room temperature overnight, and washed with water (10 ml). The solvent was removed in vacuo. Purification by semi-preparative HPLC yielded colourless solid (9 mg, 15%).

$^1$H-NMR (400 MHz, d$_6$-DMSO): δ 9.58 (br.s, if), 9.49 (br.s, 1H), 8.63 (s, 1H), 7.29 (s, 1H), 7.16 (m, 2H), 6.79 (m, 1H), 6.62 (d, J=2.6 Hz, 1H), 6.54 (dd, J=8.7, 2.5 Hz, 1H), 6.01 (br.s, 1H), 4.35 (br.s, 1H), 4.05-3.89 (m, 2), 3.75 (s, 3H), 3.67-3.15 (m, 6H), 3.10 (s, 2H), 2.87 (s, 3H), 2.24-1.95 (m, 4H)

APCI-MS: m/z 497 (MH$^+$).

Example 13

(2S)-1-(4-Bromo-2-fluorophenoxy)-3-(5-chloro-1'H,3H-spiro[1-benzofuran-2,4'-piperidin]-1'-yl)propan-2-ol A slurry of 4-bromo-2-fluorophenol (100 uL, 0.5 M in dimethylformamide), (2S)-oxiran-2-ylmethyl 3-nitrobenzenesulfonate (100 uL, 0.5 M in dimethylformamide) and caesium carbonate (13 mg, 0.04 mmol) was stirred at room temperature over night, and then partiotioned between water and dichloromethane. The organic phase was evaporated, and the resulting crude (2S)-2-[(4-bromo-2-fluorophenoxy)methyl]-oxirane was dissolved in ethanol (400 uL) and 5-chloro-3H-spiro[1-benzofuran-2,4'-piperidine] (100 uL, 0.5 M in dimethylformamide) was added. The mixture was refluxed over night, and the solvent was evaporated. Purification was performed on C18 with acetonitrile/water 0.1% trifluoroacetic acid as mobile phase. Pure fractions were collected, pooled and evaporated to give the title compound as the trifluoroacetate salt.

APCI-MS m/z: 471 [MH$^+$]

The following Examples 14 to 64 were prepared by methods analogous to the method described in Example 13.

Example 14

(2S)-1-(5-Chloro-1'H,3H-spiro[1-benzofuran-2,4'-piperidin]-1'-yl)-3-(3-ethynylphenoxy)propan-2-ol APCI-MS m/z: 398 [MH$^+$]

Example 15

(2S)-1-(5-Chloro-1'H,3H-spiro[1-benzofuran-2,4'-piperidin]-1'-yl)-3-(2,4-dichloro-3,5-dimethylphenoxy)propan-2-ol APCI-MS m/z: 470 [MH$^+$]

Example 16

(2S)-1-(4-Chloro-2-isoxazol-5-ylphenoxy)-3-(5-chloro-1'H,3H-spiro[1-benzofuran-2,4'-piperidin]-1'-yl)propan-2-ol APCI-MS m/z: 475 [MH$^+$]

Example 17

(4-{[(2S)-3-(5-Chloro-1'H,3H-spiro[1-benzofuran-2,4'-piperidin]-1'-yl)-2-hydroxypropyl]oxy}phenyl)(phenyl)methanone APCI-MS m/z: 478 [MH$^+$]

Example 18

(2S)-1-(5-Chloro-1'H,3H-spiro[1-benzofuran-2,4'-piperidin]-1'-yl)-3-(2,3,4,6-tetrachlorophenoxy)propan-2-ol APCI-MS m/z: 510 [MH$^+$]

Example 19

(2S)-1-(5-Chloro-1'H,3H-spiro[1-benzofuran-2,4'-piperidin]-1'-yl)-3-(2-cyclohexyl-5-methylphenoxy)propan-2-ol APCI-MS m/z: 470 [MH$^+$]

Example 20

(2S)-1-(5-Chloro-1'H,3H-spiro[1-benzofuran-2,4'-piperidin]-1'-yl)-3-phenoxypropan-2-ol APCI-MS m/z: 374 [MH$^+$]

Example 21

(2S)-1-(2-Bromophenoxy)-3-(5-chloro-1'H,3H-spiro[1-benzofuran-2,4'-piperidin]-1'-yl)propan-2-ol APCI-MS m/z: 453 [MH$^+$]

Example 22

2-{([(2S)-3-(5-Chloro-1'H,3H-spiro[1-benzofuran-2,4'-piperidin]-1'-yl)-2-hydroxypropyl]oxy}benzaldehyde APCI-MS m/z: 402 [MH$^+$]

Example 23

5-tert-Butyl-2-{[(2S)-3-(5-chloro-1'H,3H-spiro[1-benzofuran-2,4'-piperidin]-1'-yl)-2-hydroxypropyl]oxy}benzaldehyde APCI-MS m/z: 458 [MH$^+$]

Example 24

(2S)-1-(5-Chloro-1'H,3H-spiro[1-benzofuran-2,4'-piperidin]-1'-yl)-3-(1,1':3',1''-terphenyl-2'-yloxy)propan-2-ol APCI-MS m/z: 526 [MH$^+$]

Example 25

1-(2-{[(2S)-3-(5-Chloro-1'H,3H-spiro[1-benzofuran-2,4'-piperidin]-1'-yl)-2-hydroxypropyl]oxy}-5-methoxyphenyl)ethanone APCI-MS m/z: 446 [MH$^+$]

Example 26

1-(5-Bromo-2-{[(2S)-3-(5-chloro-1'H,3H-spiro[1-benzofuran-2,4'-piperidin]-1'-yl)-2-hydroxypropyl]oxy}phenyl)ethanone APCI-MS m/z: 495 [MH$^+$]

Example 27

(2S)-1-(4-Chloro-2-isopropyl-5-methylphenoxy)-3-(5-chloro-1'H,3H-spiro[1-benzofuran-2,4'-piperidin]-1'-yl)propan-2-ol APCI-MS m/z: 464 [MH$^+$]

Example 28

(2S)-1-(5-Chloro-1'H,3H-spiro[1-benzofuran-2,4'-piperidin]-1'-yl)-3-(2,3-dimethyl-4-nitrophenoxy)propan-2-ol APCI-MS m/z: 447 [MH$^+$]

Example 29

(2S)-1-(5-Chloro-1'H,3H-spiro[1-benzofuran-2,4'-piperidin]-1'-yl)-3-(2,4-dichlorophenoxy)propan-2-ol APCI-MS m/z: 442 [MH$^+$]

Example 30

Ethyl (2E)-3-(4-{[(2S)-3-(5-chloro-1'H,3H-spiro[1-benzofuran-2,4'-piperidin]-1'-yl)-2-hydroxypropyl]oxy}-3-methoxyphenyl)acrylate APCI-MS m/z: 502 [MH$^+$]

Example 31

(2S)-1-(5-Chloro-1'H,3H-spiro[1-benzofuran-2,4'-piperidin]-1'-yl)-3-(2-methyl-3-nitrophenoxy)propan-2-ol APCI-MS m/z: 433 [MH$^+$]

Example 32

5-Chloro-2-{[(2S)-3-(5-chloro-1'H,3H-spiro[1-benzofuran-2,4'-piperidin]-1'-yl)-2-hydroxypropyl]oxy}benzaldehyde APCI-MS m/z: 436 [MH$^+$]

Example 33

(2S)-1-(5-Chloro-1'H,3H-spiro[1-benzofuran-2,4'-piperidin]-1'-yl)-3-(2-fluorophenoxy)propan-2-ol APCI-MS m/z: 392 [MH$^+$]

Example 34

(2S)-1-(5-Chloro-1'H,3H-spiro[1-benzofuran-2,4'-piperidin]-1'-yl)-3-(3-fluorophenoxy)propan-2-ol APCI-MS m/z: 392 [MH+]

Example 35

(2S)-1-(5-Chloro-1'H,3H-spiro[1-benzofuran-2,4'-piperidin]-1'-yl)-3-(4-fluorophenoxy)propan-2-ol APCI-MS m/z: 392[MH+]

Example 36

(2S)-1-(2-Chlorophenoxy)-3-(5-chloro-1'H,3H-spiro[1-benzofuran-2,4'-piperidin]-1'-yl)propan-2-ol APCI-MS m/z: 408 [MH+]

Example 37

(2S)-1-(3-Chlorophenoxy)-3-(5-chloro-1'H,3H-spiro[1-benzofuran-2,4'-piperidin]-1'-yl)propan-2-ol APCI-MS m/z: 408 [MH+]

Example 38

(2S)-1-(4-Chlorophenoy)-3-(5-chloro-1'H,3H-spiro[1-benzofuran-2,4'-piperidin]-1'-yl)propan-2-ol APCI-MS m/z: 408 [MH+]

Example 39

(2S)-1-(3-Bromophenoy)-3-(5-chloro-1'H,3H-spiro[1-benzofuran-2,4'-piperidin]-1'-yl)propan-2-ol APCI-MS m/z: 453 [MH+]

Example 40

(2S)-1-(4-Bromophenoxy)-3-(5-chloro-1'H,3H-spiro[1-benzofuran-2,4'-piperidin]-1'-yl)propan-2-ol APCI-MS m/z: 453 [MH+]

Example 41

(2S)-1-(2-tert-Butyl-5-methylphenoxy)-3-(5-chloro-1'H,3H-spiro[1-benzofuran-2,4'-piperidin]-1'-yl)propan-2-ol APCI-MS m/z: 444 [MH+]

Example 42

(2S)-1-(5-Chloro-1'H,3H-spiro[1-benzofuran-2,4'-piperidin]-1'-yl)-3-[2-(trifluoromethyl)phenoxy]propan-2-ol APCI-MS m/z: 442 [MH+]

Example 43

1-(2-{[(2S)-3-(5-Chloro-1'H,3H-spiro[1-benzofuran-2,4'-piperidin]-1'-yl)-2-hydroxypropyl]oxy}-4,5-dimethoxyphenyl)ethanone APCI-MS m/z: 476 [MH+]

Example 44

(2S)-1-(5-Chloro-1'H,3H-spiro[1-benzofuran-2,4'-piperidin]-1'-yl)-3-[2,3,5,6-tetrafluoro-4-(trifluoromethyl)phenoxy]propan-2-ol APCI-MS m/z: 514 [MH+]

Example 45

(2S)-1-(4-Chloro-3-ethylphenoxy)-3-(5-chloro-1'H,3H-spiro[1-benzofuran-2,4'-piperidin]-1'-yl)propan-2-ol APCI-MS m/z: 436 [MH+]

Example 46

(2S)-1-(5-Chloro-1'H,3H-spiro[1-benzofuran-2,4'-piperidin]-1'-yl)-3-[3-(2,5-dimethyl-1H-pyrrol-1-yl)phenoxy]propan-2-ol APCI-MS m/z: 467 [MH+]

Example 47

(2S)-1-(5-Chloro-1'H,3H-spiro[1-benzofuran-2,4'-piperidin]-1'-yl)-3-[2-(hydroxymethyl)phenoxy]propan-2-ol APCI-MS m/z: 404 [MH+]

Example 48

(2S)-1-(5-Chloro-1'H,3H-spiro[1-benzofuran-2,4'-piperidin]-1'-yl)-3-[2-(2-hydroxyethyl)phenoxy]propan-2-ol APCI-MS m/z: 418 [MH+]

Example 49

3-{[(2S)-3-(5-Chloro-1'H,3H-spiro[1-benzofuran-2,4'-piperidin]-1'-yl)-2-hydroxypropyl]oxy}benzonitrile APCI-MS m/z: 399 [MH+]

Example 50

2-{[(2S)-3-(5-Chloro-1'H,3H-spiro[1-benzofuran-2,4'-piperidin]-1'-yl)-2-hydroxypropyl]oxy}benzonitrile APCI-MS m/z: 399 [MH+]

Example 51

(2S)-1-(5-Chloro-1'H,3H-spiro[1-benzofuran-2,4'-piperidin]-1'-yl)-3-(2-morpholin-4-ylphenoxy)propan-2-ol APCI-MS m/z: 459 [MH$^+$]

Example 52

(2S)-1-(5-Chloro-1'H,3H-spiro[1-benzofuran-2,4'-piperidin]-1'-yl)-3-(2,3-difluoro-6-nitrophenoxy)propan-2-ol APCI-MS m/z: 455 [MH$^+$]

Example 53

(2S)-1-(5-Chloro-1'H,3H-spiro[1-benzofuran-2,4'-piperidin]-1'-yl)-3-(2,3,6-trichlorophenoxy)propan-2-ol APCI-MS m/z: 476 [MH$^+$]

Example 54

(2S)-1-(5-Chloro-1'H,3H-spiro[1-benzofuran-2,4'-piperidin]-1'-yl)-3-(4-fluoro-2-methoxyphenoxy)propan-2-ol APCI-MS m/z: 422[MH$^+$]

Example 55

5-Chloro-2-{[(2S)-3-(5-chloro-1'H,3H-spiro[1-benzofuran-2,4'-piperidin]-1'-yl)-2-hydroxypropyl]oxy}-3-methylbenzaldehyde APCI-MS m/z: 450 [MH$^+$]

Example 56

(2S)-1-(5-Chloro-1'H,3H-spiro[1-benzofuran-2,4'-piperidin]-1'-yl)-3-[4-(4-methylpiperidin-1-yl)-2-nitrophenoxy]propan-2-ol APCI-MS m/z: 517 [MH$^+$]

Example 57

(2S)-1-(5-Chloro-1'H,3H-spiro[1-benzofuran-2,4'-piperidin]-1'-yl)-3-(2,4-dichloro-3,5-dim ethyl-6-nitrophenoxy)propan-2-ol APCI-MS m/z: 514 [MH$^+$]

Example 58

1-(3,5-Dichloro-2-{[(2S)-3-(5-chloro-1'H,3H-spiro[1-benzofuran-2,4'-piperidin]-1'-yl)-2-hydroxypropyl]oxy}phenyl)propan-1-one APCI-MS m/z: 498 [MH$^+$]

Example 59

(2S)-1-(5-Chloro-1'H,3H-spiro[1-benzofuran-2,4'-piperidin]-1'-yl)-3-(4-ethylphenoxy)propan-2-ol APCI-MS m/z: 402 [MH$^+$]

Example 60

(2S)-1-(5-Chloro-1'H,3H-spiro[1-benzofuran-2,4'-piperidin]-1'-yl)-3-(2-ethylphenoxy)propan-2-ol APCI-MS m/z: 402 [MH$^+$]

Example 61

(2S)-1-(5-Chloro-1'H,3H-spiro[1-benzofuran-2,4'-piperidin]-1'-yl)-3-(3-ethylphenoxy)propan-2-ol APCI-MS m/z: 402 [MH$^+$]

Example 62

(2S)-1-(5-Chloro-1'H,3H-spiro[1-benzofuran-2,4'-piperidin]-1'-yl)-3-(3-morpholin-4-ylphenoxy)propan-2-ol APCI-MS m/z: 459 [MH$^+$]

Example 63

(2S)-1-(5-Chloro-1'H,3H-spiro[1-benzofuran-2,4'-piperidin]-1'-yl)-3-[2-(5-methyl-1,3,4-oxadiazol-2-yl)phenoxy]propan-2-ol APCI-MS m/z: 456 [MH$^+$]

Example 64

4-{[(2S)-3-(5-Chloro-1'H,3H-spiro[1-benzofuran-2,4'-piperidin]-1'-yl)-2-hydroxypropyl]oxy}benzonitrile APCI-MS m/z: 399 [MH$^+$]

Example 65

(2S)-1-(5-chloro-1'H,3H-spiro[1-benzofuran-2,4'-piperidin]-1'-yl)-3-[2-(pyrrolidin-1-ylsulfonyl)phenoxy]propan-2-ol Step I:

2-(pyrrolidin-1-ylsulfonyl)phenol

To a solution of 4-tert-butyl-2-methoxybenzenesulfonyl chloride (258 mg, 0.99 mmol) in DMF (6 ml) was added pyrrolidine (70 mg, 0.99 mmol) and the solution was stirred at ambient temperature for 30 minutes, and concentrated in vacuo. The residue was dissolved in xylene (10 ml) and then added to mixture of AlCl$_3$ (525 mg, 3.39 mmol) in xylene (5 ml). The resulting mixture was stirred for 18 h at 70° C. After colling the mixture was poured into stirred ice-cold water, and extracted with ether (2×30 ml). The ether layer was dried over sodium sulfate, filtered and concentrated to give 120 mg of subtitle compound.

$^1$H-NMR (400 MHz, D$_2$O): δ 7.64 (1H, m); 7.41(1H, m); 6.95 (2H, m); 3.22 (4H, m); 1.85 (4H, m)

APCI-MS m/z: 228.1 [MH$^+$]

Step II:

1-({2-[(2R)-oxiran-2-ylmethoxy]phebyl}sulphonyl)pyrrolidine

Prepared from 2-(pyrrolidin-1-ylsulfonyl)phenol as described in Example 1, Step 1.
APCI-MS m/z: 284.2 [MH⁺]

Step III:

(2S)-1-(5-chloro-1'H,3H-spiro[1-benzofuran-2,4'-piperidin]-1'-yl)-3-[2-(pyrrolidin-1-ylsulfonyl)phenoxy]propan-2-ol Prepared from 1-({2-[(2R)-oxiran-2-ylmethoxy]phebyl}sulphonyl)pyrrolidine as described in Example 1, Step 2.
$^1$H-NMR (400 MHz, D$_2$O): δ 7.83 (1H, m); 7.55(1H, m); 7.16 (H, s); 7.09(3H, m); 6.75 (1H, d; J=9 Hz); 4.57(1H, m); 4.18(2H, m); 3.7(1H, m); 3.59(2H, m); 3.35(6H, m); 3.10 (1H, M); 2.33(2H, m); 2.14(2H, m); 1.80(4H, m).
APCI-MS m/z: 507 [MH⁺]

Example 66

1-(2-{[(2S)-3-(5-chloro-1'H,3H-spiro[1-benzofuran-2,4'-piperidin]-1'-yl)-2-hydroxypropoxy]benzyl}imidazoline-2,4-dione Step I:

2-[(2S)-oxiran-2-ylmethoxy]benzaldehyde

Salicylaldehyde (486 mg, 3.99 mmol) and (2S)-oxiran-2-ylmethyl 3-nitrobenzenesulfonate (900 mg, 3.47 mmol) was dissolved in DMF (5 ml) and Cs$_2$CO$_3$ (1.28 g, 3.94 mmol) was added. The reaction mixture stirred for 12 at room temperature. Water (100 ml) was added, and the mixture was extracted with DCM (2×50 ml). The combined organic extracts were washed with water (2×50 ml). The volatiles were removed in vacuo to give the subtitle compound (76%, 710 mg), which was used directly in the next step.
APCI-MS: m/z 179 (MH⁺)

Step II:

2-{[(2S)-3-(5-chloro-1'H,3H-spiro[1-benzofuran-2,4'-piperidin]1'-yl)-2-hydroxypropyl]oxy}benzaldehyde A mixture of 5-chloro-3H-spiro[1-benzofuran-2,4'-piperidine] (889 mg, 3.99 mmol) and 2-[(2S)-oxiran-2-ylmethoxy]benzaldehyde (710 mg, 3.99 mmol) in EtOH (30 ml) was heated at 80° C. for 12 h. The volatiles were removed in vacuo and the residue was purifired by flash cromatography (silica gel, CH$_2$Cl$_2$:MeOH, 10:1) to give the subtitle compound (60%, 933 mg).
APCI-MS: m/z 402 (MH⁺)

Step III:

Ethyl N-(2-{[(2S)-3(5-chloro-1'H,3H-spiro[1-benzofuran-2,4'-piperidin]1'-yl)-2-hydroxypropyl]oxy}benzaldehyd)glycinate A mixture of 2-{[(2S)-3-(5-chloro-1'H,3H-spiro[1-benzofuran-2,4'-piperidin]1'-yl)-2-hydroxypropyl]oxy}benzaldehyde (933 mg, 2.41 mmol) and ethyl glycinate hydrochloride (335 mg, 2.41 mmol) and NaCNBH$_4$ (302 mg, 4.28 mmol) in EtOH/THF (1:1, 30 ml) was stirred in room temperature at pH 4 (adjusted by addition of acetic acid) for 1.5 h. The volatiles were removed in vacuo, and the residue was purified by flash chromatography (silica gel, CH$_2$Cl$_2$:MeOH, 10:1) to give the subtitle compound (37%, 435 mg).
APCI-MS: m/z 490 (MH⁺)

Step IV:

1-(2-{[(2S)-3-(5-chloro-1'H,3H-spiro[1-benzofuran-2,4'-piperidin]-1'-yl)-2-hydroxypropoxy]benzyl}imidazoline-2,4-dione Ethyl N-(2-{[(2S)-3-(5-chloro-1'H,3H-spiro[1-benzofuran-2,4'-piperidin]1'-yl)-2-hydroxypropyl]oxy}benzaldehyde)glycinate (435 mg, 0.89 mmol) was dissolved in 1M HCl (0.975 ml) and KOCN (109 mg, 1.33 mmol) was added. The reaction mixture was heated to 90° C. for 10 min. Conc. HCl (1.11 ml) was added, and the reaction mixture was heated at 100° C. for 0.5 h. The volatiles were removed in vacuo, and the residue was purified by flash chromatography (silica gel, CH$_2$Cl$_2$:MeOH, 10:1) and HPLC to give the title compound (35%, 152 mg).
$^1$H-NMR (acetone-d$_6$, 400 MHz): δ 7.28-7.34 (m, 2H); 6.92-7.19 (m, 4H); 6.67-6.73 is (m, 1H); 4.55-4.60 (m, 2H); 3.95-4.5 (m, 3H); 3.80-3.85 (m, 2H); 3.05-3.15 (m, 2H); 2.65-2.85 (m, 6H); 1.56-1.95 (m, 4H).
APCI-MS: m/z 486(MH⁺)

Example 67

(2S)-{2-chloro-5-[3-(5-chloro-1'H,3H-spiro[1-benzofuran-2,4'-piperidin]-1'-yl)-2-hydroxypropoxy]phenoxy}acetic acid Step I:

(2S)-2-[(4-chloro-3-methoxyphenoxy)methyl]oxirane

Sodium nitrite (5 g) in water was added to a solution of 2-chloro-5-amino-anisole (10 g) in sulfuric acid (3%, 50 ml) at 50° C. Stirred for 1 h and then heated at reflux for 1 h. The solution was cooled and extracted with ethyl acetate, which was dried (Na$_2$SO$_4$) and concentrated in vacuo. To the resultant gum was added (2S)-oxiran-2-ylmethyl 3-nitrobenzenesulfonate (1.6 g) and caesium carbonate (2 g) in THF (10 ml) and the mixture was stirred at 50° C. overnight. The mixture was concentrated, water was added and extracted with ethyl acetate. The combined organic layers were dried with sodium sulphate and the volatiles were removed in vacuo. Purification by column chromatography (ethyl acetate:isohexanes 1:4) gave the title compound as an orange oil (0.42 g).
GCMS: m/z 214 (MH+)

Step II:

(2S)-{2-chloro-5-[3-(5-chloro-1'H,3H-spiro[1-benzofuran-2,4'-piperidin]-1'-yl)-2-hydroxypropoxy]phenoxy}acetic acid A mixture of 5-chloro-3H-spiro[1-benzofuran-2,4'-piperidine] (0.6 g) and (2S)-2-[(4-chloro-3-methoxyphenoxy)methyl]oxirane (1 g) in ethanol (10 mL) was stirred at 60° C. overnight. The volatiles were removed in vacuo and the residue was purified by column chromatography (ethyl acetate:isohexanes:ethanol, 1:1:0 to 20:0:1) to give a gum (0.6 g). The gum was dissolved in DCM (10 ml) and treated with BBr$_3$ (1M in DCM; 2 ml) at r.t. for 1 h. Methanol (1 ml) was added and stirred for 1 h then concentrated in vacuo to leave the phenol intermediate. This phenol (0.6 g) was added to a mixture of potassium carbonate (0.5 g) and methyl bromoacetate (0.24 g) in THF (10 ml) and heated at reflux for 4 h. The mixture was cooled and methanol (10 ml) was added followed by lithium hydroxide (20 mg). The mixture was stirred at r.t for 3 h and then concentrated in vacuo. Methanol (2 ml) was added and the mixture was filtered and the filtrate purified by reverse phase HPLC (Xterra, gradient 75-5% aqueous ammonia (0.2% aq.) in acetonitrile) to give the title compound as a white solid (40 mg).

$^1$H-NMR (CDCl3, 400 MHz): δ 7.30 (d, 1H); 7.23 (s, 1H); 7.1 (dd, 1H); 6.74 (d, 1H); 6.54-6.57 (m, 2H); 4.71 (s, 2H); 3.90-4.02 (m, 2H); 3.82 (tt, 1H); 3.00 (s, 2H); 2.50-2.80 (m, 6H); 1.70-1.90 (m, 4H)

APCI-MS: m/z 480(M-H$^+$)

Example 68

(2S)-{2,4-dichloro-5-[3-(5-chloro-1'H,3H-spiro[1-benzofuran-2,4'-piperidin]-1'-yl)-2-hydroxypropoxy] phenoxy}acetic acid Step I:

Methyl (2,4-dichloro-5-hydroxyphenoxy)acetate

A mixture of 4,6-dichlororesorcinol (2 g), potassium carbonate (1.54 g) and methyl bromoacetate (1.71 g) in DMF (10 ml) was heated at 80° C. for 24 h. The resulting mixture was cooled and water (200 ml) added. Solid (bis-alkylated product) was filtered off, then the aqueous was acidified with aq. HCl, which was extracted with ether and the organics were dried and concentrated in vacuo. Purification by RPHPLC (Xterra, gradient 95-5%, ammonia (0.2% aq.) in acetonitrile) gave the subtitle compound (0.65 g) as a solid.

APCI-MS: m/z 250(M+H$^-$)

Step I:

(2S)-{2,4-dichloro-5-[3-(5-chloro-1'H,3H-spiro[1-benzofuran-2,4'-piperidin]-1'-yl)-2-hydroxypropoxy] phenoxy}acetic acid A mixture of (2S)-oxiran-2-ylmethyl-3-nitrobenzenesulfonate (0.4 g), methyl (2,4-dichloro-5-hydroxyphenoxy) acetate (0.39 g) and Cs$_2$CO$_3$ (0.58 g) in DMF (2 ml) was stirred at r.t. overnight. Water was added and (2,4-dichloro-5-oxiranylmethoxy-phenoxy)-acetic acid methyl ester (0.22 g) was isolated by filtration and dried in vacuo. 5-Chloro-3H-spiro[1-benzofuran-2,4'-piperidine] (0.16 g) in ethanol (5 ml) was added and heated at 70° C. for 2 h. The mixture was allowed to cool and water (1 ml) followed by LiOH (2 eq) was added. Stirred for 3 h. RPHPLC (Xterra, gradient 95-5%, ammonia (0.2% aq.): acetonitrile) gave the title compound (0.1 g) as a white solid.

1H NMR (DMSO 300 MHz) δ 7.40(s, 1H); 7.22 (d, J=2.1 Hz, 1H); 7.09(dd, J=8.5, 2.3 Hz, 1H); 6.75 (d, J=8.5 Hz, 1H); 6.64 (s, 1H); 4.93 (s, 1H); 4.22 (s, 2H); 4.01-3.85 (m, 3H); 2.99 (s, 2H); 2.66-2.35 (m, 6H); 1.87-1.67 (m, 4H)

APCI-MS: m/z 514 (M-H$^+$)

THP-1 Chemotaxis Assay

Introduction

The assay measures the chemotactic response elicited by MIP-1α chemokine in the human monocytic cell line THP-1. Compounds are evaluated by their ability to depress the chemotactic response to a standard concentration of MIP-1α chemokine.

Methods

Culture of THP-1 Cells

Cells are thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is $4 \times 10^5$ cells/ml.

Chemotaxis Assay

Cells are removed from the flask and washed by centrifugation in RPMI+110% HIFCS+glutamax. The cells are then resuspended at $2 \times 10^7$ cells/ml in fresh medium (RPMI+10% HIFCS+glutamax) to which is added calcein-AM (5 μl of stock solution to 1 ml to give a final concentration of $5 \times 10^{-6}$ M). After gentle mixing the cells are incubated at 37° C. in a $CO_2$ incubator for 30 minutes. The cells are then diluted to 50 ml with medium and washed twice by centrifugation at 400× g. Labelled cells are then resuspended at a cell concentration of $1 \times 10^7$ cells/ml and incubated with an equal volume of MIP-1α antagonist ($10^{-10}$ M to $10^{-6}$ M final concentration) for 30 minutes at 37° C. in a humidified $CO_2$ incubator.

Chemotaxis is performed using Neuroprobe 96-well chemotaxis plates employing 8 μm filters (cat no. 101-8). Thirty microlitres of chemoattractant supplemented with various concentrations of antagonists or vehicle are added to the lower wells of the plate in triplicate. The filter is then carefully positioned on top and then 25 μl of cells preincubated with the corresponding concentration of antagonist or vehicle is added to the surface of the filter. The plate is then incubated for 2 hours at 37° C. in a humidified $CO_2$ incubator. The cells remaining on the surface are then removed by adsorption and the whole plate is centrifuged at 2000 rpm for 10 minutes. The filter is then removed and the cells that have migrated to the lower wells are quantified by the fluorescence of cell associated calcein-AM. Cell migration is then expressed in fluorescence units after subtraction of the reagent blank and values are standardized to % migration by comparing the fluorescence values with that of a known number of labelled cells. The effect of antagonists is calculated as % inhibition when the number of migrated cells is compared with vehicle.

The invention claimed is:

1. A compound of formula

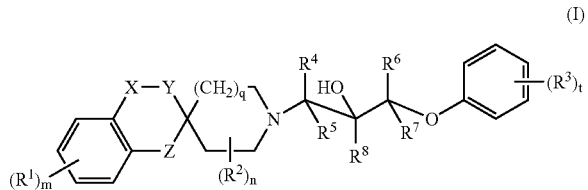

(I)

wherein
   m is 0, 1, 2, 3 or 4;
      each $R^1$ independently represents halogen, cyano, hydroxyl, $C_1$-$C_6$alkyl, $C_1$-$C_6$ haloalkyl, $C_1$-$C_6$ alkoxy or sulphonamido;
   X represents a bond, —$CH_2$— or —O—, Y represents a bond, —$CH_2$— or —O—, and Z represents a bond, —O—, —NH— or —$CH_2$—, provided that only one of X, Y and Z can represent a bond at any one time and provided that X and Y do not both simultaneously represent —O—;
   n is 0, 1 or 2;
      each $R^2$ independently represents halogen, $C_1$-$C_6$ alkyl or $C_1$-$C_6$ haloalkyl;
   q is 0 or 1;
   t is 0, 1, 2, 3, 4 or 5;
      each $R^3$ independently represents halogen, cyano, nitro, hydroxyl, —C(O)H, —$NR^9R^{10}$, —$CH_2$C(O)$NR^{11}R^{12}$, —$CH_2$NHC(O)$R^{13}$, —$NHSO_2R^{14}$, —$SO_2NR^{15}R^{16}$, —$CH_2$—$R^{17}$, $C_1$-$C_6$ alkylcarbonyl, phenylcarbonyl, $C_3$-$C_6$ cycloalkyl, or a group selected from $C_1$-$C_6$ alkyl, $C_2$-$C_6$ alkenyl, $C_2$-$C_6$ alkynyl, $C_1$-$C_6$ alkoxy, phenyl and a saturated or unsaturated 5- to 10-membered heterocyclic ring system comprising at least one ring heteroatom selected from nitrogen, oxygen and sulphur, each group being optionally substituted with at least one substituent selected from halogen, cyano, hydroxyl, carboxyl, $C_1$-$C_6$ alkyl, $C_1$-$C_6$ alkoxy and $C_1$-$C_6$ alkoxycarbonyl;
   $R^4$, $R^5$, $R^6$, $R^7$ and $R^8$ each independently represent hydrogen, halogen, $C_1$-$C_6$ alkyl or $C_1$-$C_6$ haloalkyl;
   $R^9$ and $R^{10}$ each independently represent hydrogen or $C_1$-$C_6$ alkyl;
   $R^{11}$ and $R^{12}$ each independently represent hydrogen or $C_1$-$C_6$ alkyl, or $R^{11}$ and $R^{12}$ together with the nitrogen atom to which they are attached form a 4- to 7-membered saturated heterocyclic ring which may be optionally substituted with at least one substituent selected from hydroxyl;
   $R^{13}$ and $R^{14}$ each independently represent hydrogen or $C_1$-$C_6$ alkyl; and
   $R^{15}$ and $R^{16}$ each independently represent hydrogen or $C_1$-$C_6$ alkyl, or $R^{15}$ and $R^{16}$ together with the nitrogen atom to which they are attached form a 4- to 7-membered saturated heterocyclic ring which may be optionally substituted with at least one substituent selected from hydroxyl;
   $R^{17}$ is a 5 to 7 membered saturated heterocyclic ring containing at least one nitrogen atom, which ring may be optionally substituted with one or more oxo groups;
or a pharmaceutically acceptable salt thereof.

2. A compound according to claim 1, wherein X and Y have the meanings shown in the following table:

| X | Y |
|---|---|
| bond | O |
| O | bond |
| $CH_2$ | bond |
| bond | $CH_2$ |

3. A compound according to claim 1, wherein Z represents —O— or —$CH_2$—.

4. A compound according to claim 1, wherein q is 1.

5. A compound according to claim 1, wherein m is 1 and $R^1$ represents halogen.

6. A compound according to claim 1, wherein each $R^3$ independently represents halogen, cyano, nitro, hydroxyl, —C(O)H, —$NR^9R^{10}$, —$CH_2$C(O)$NR^{11}R^{12}$, —$CH_2$NHC(O)$R^{13}$, —$NHSO_2R^{14}$, —$SO_2NR^{15}R^{16}$, —$CH_2$—$R^{17}$, $C_1$-$C_4$ alkylcarbonyl, phenylcarbonyl, $C_5$-$C_6$ cycloalkyl or a group selected from $C_1$-$C_4$ alkyl, $C_2$-$C_4$ alkenyl, $C_2$-$C_4$ alkynyl, $C_1$-$C_4$ alkoxy, phenyl and a saturated or unsaturated 5- to 6-membered heterocyclic ring system comprising one, two, three or four ring heteroatoms independently selected from nitrogen, oxygen and sulphur, each group being optionally substituted with one, two, three or four substituents independently selected from halogen, cyano, hydroxyl, carboxyl, $C_1$-$C_4$ alkyl, $C_1$-$C_4$ alkoxy and $C_1$-$C_4$ alkoxycarbonyl.

7. A compound according to claim 6, wherein the saturated or unsaturated 5- to 6-membered heterocyclic ring system is isoxazolyl, pyrrolyl, morpholinyl, piperidinyl or oxadiazolyl.

8. A compound according to claim 1 selected from:
   (2S)-1-(5-Chloro-1'H,3H-spiro[1-benzofuran-2,4'-piperidin]-1'-yl)-3-(2-methoxyphenoxy)propan-2-ol hydrochloride,
   2-{[(2S)-3-(5-Chloro-1'H,3H-spiro[1-benzofuran-2,4'-piperidin]-1'-yl)-2-hydroxypropyl]oxy}phenol,
   (2S)-1-(5-Chloro-1'H,3H-spiro[1-benzofuran-2,4'-piperidin]-1'-yl)-3-[2-(2-hydroxyethoxy)phenoxy]propan-2-ol hydrochloride,
   2-(2-{[(2S)-3-(5-Chloro-1'H,3H-spiro[1-benzofuran-2,4'-piperidin]-1'-yl)-2-hydroxypropyl]oxy}phenyl)-N-methylacetamide trifluoroacetate (salt),
   (3S)-1-[(2-{[(2S)-3-(5-Chloro-1'H,3H-spiro[1-benzofuran-2,4'-piperidin]-1'-yl)-2-hydroxypropyl]oxy}phenyl)acetyl]pyrrolidin-3-ol,
   N-(2-{[(2S)-3-(5-Chloro-1'H,3H-spiro[1-benzofuran-2,4'-piperidin]-1'-yl-2-hydroxypropyl]oxy}benzyl)acetamide,
   2-(2-{[(2S)-3-(5-Chloro-1'H,3H-spiro[1-benzofuran-2,4'-piperidin]-1'-yl)-2-hydroxypropyl]oxy}-4-methoxyphenyl)-N-methylacetamide,
   2-(2-{[(2S)-3-(5-Chloro-1'H,3H-spiro[1-benzofuran-2,4'-piperidin]-1'-yl)-2-hydroxypropyl]oxy}-4-hydroxyphenyl)-N-methylacetamide trifluoroacetate (salt),
   2-(4-{[(2S)-3-(5-Chloro-1'H,3H-spiro[1-benzofuran-2,4'-piperidin]-1'-yl)-2-hydroxypropyl]oxy}-2-methoxyphenyl)-N-methylacetamide,
   (2S)-1-(2-Amino-5-methoxyphenoxy)-3-(5-chloro-1'H,3H-spiro[1-benzofuran-2,4'-piperidin]-1'-yl)propan-2-ol bis(trifluoroacetate),
   N-(2-{[(2S)-3-(5-Chloro-1'H,3H-spiro[1-benzofuran-2,4'-piperidin]-1'-yl)-2-hydroxypropyl]oxy}-4-hydroxyphenyl)methanesulfonamide trifluoroacetate,
   N-(2-{[(2S)-3-(5-Chloro-1'H,3H-spiro[1-benzofuran-2,4'-piperidin]-1'-yl)-2-hydroxypropyl]oxy}-4-methoxyphenyl)methanesulfonamide trifluoroacetate,
   (2S)-1-(4-Bromo-2-fluorophenoxy)-3-(5-chloro-1'H,3H-spiro[1-benzofuran-2,4'-piperidin]-1'-yl)propan-2-ol,
   (2S)-1-(5-Chloro-1'H,3H-spiro[1-benzofuran-2,4'-piperidin]-1'-yl)-3-(3-ethynylphenoxy)propan-2-ol,
   (2S)-1-(5-Chloro-1'H,3H-spiro[1-benzofuran-2,4'-piperidin]-1'-yl)-3-(2,4-dichloro-3,5-dimethylphenoxy)propan-2-ol,
   (2S)-1-(4-Chloro-2-isoxazol-5-ylphenoxy)-3-(5-chloro-1'H,3H-spiro[1-benzofuran-2,4'-piperidin]-1'-yl)propan-2-ol,
   (4-{[(2S)-3-(5-Chloro-1'H,3H-spiro[1-benzofuran-2,4'-piperidin]-1'-yl)-2-hydroxypropyl]oxy}phenyl)(phenyl)methanone, (2S)-1-(5-Chloro-1'H,3H-spiro[1-benzofuran-2,4'-piperidin]-1'-yl)-3-(2,3,4,6-tetrachlorophenoxy)propan-2-ol,
(2S)-1-(5-Chloro-1'H,3H-spiro[1-benzofuran-2,4'-piperidin]-1'-yl)-3-(2-cyclohexyl-5-methylphenoxy)propan-2-ol,
(2S)-1-(5-Chloro-1'H,3H-spiro[1-benzofuran-2,4'-piperidin]-1'-yl)-3-phenoxypropan-2-ol,
(2S)-1-(2-Bromophenoxy)-3-(5-chloro-1'H,3H-spiro[1-benzofuran-2,4'-piperidin]-1'-yl)propan-2-ol,
2-{[(2S)-3-(5-Chloro-1'H,3H-spiro[1-benzofuran-2,4'-piperidin]-1'-yl)-2-hydroxypropyl]oxy}benzaldehyde,
5-tert-Butyl-2-{[(2S)-3-(5-chloro-1'H,3H-spiro[1-benzofuran-2,4'-piperidin]-1'-yl)-2-hydroxypropyl]oxy}benzaldehyde,
(2S)-1-(5-Chloro-1'H,3H-spiro[1-benzofuran-2,4'-piperidin]-1'-yl)-3-(1,1':3',1''-terphenyl-2'-yloxy)propan-2-ol,
1-(2-{[(2S)-3-(5-Chloro-1'H,3H-spiro[1-benzofuran-2,4'-piperidin]-1'-yl)-2-hydroxypropyl]oxy}-5-methoxyphenyl)ethanone,
1-(5-Bromo-2-{[(2S)-3-(5-chloro-1'H,3H-spiro[1-benzofuran-2,4'-piperidin]-1'-yl)-2-hydroxypropyl]oxy}phenyl)ethanone,
(2S)-1-(4-Chloro-2-isopropyl-5-methylphenoxy)-3-(5-chloro-1'H,3H-spiro[1-benzofuran-2,4'-piperidin]-1'-yl)propan-2-ol,
(2S)-1-(5-Chloro-1'H,3H-spiro[1-benzofiiran-2,4'-piperidin]-1'-yl)-3-(2,3-dimethyl-4-nitrophenoxy)propan-2-ol,
(2S)-1-(5-Chloro-1'H,3H-spiro[1-benzofuran-2,4'-piperidin]-1'-yl)-3-(2,4-dichlorophenoxy)propan-2-ol,
Ethyl (2E)-3-(4-{[(2S)-3-(5-chloro-1'H,3H-spiro[1-benzofuran-2,4'-piperidin]-1'-yl)-2-hydroxypropyl]oxy}-3-methoxyphenyl)acrylate,
(2S)-1-(5-Chloro-1'H,3H-spiro[1-benzofuran-2,4'-piperidin]-1'-yl)-3-(2-methyl-3-nitrophenoxy)propan-2-ol,
5-Chloro-2-{[(2S)-3-(5-chloro-1'H,3H-spiro[1-benzofuran-2,4'-piperidin]-1'-yl)-2-hydroxypropyl]oxy}benzaldehyde,
(2S)-1-(5-Chloro-1'H,3H-spiro[1-benzofuran-2,4'-piperidin]-1'-yl)-3-(2-fluorophenoxy)propan-2-ol,
(2S)-1-(5-Chloro-1'H,3H-spiro[1-benzofuran-2,4'-piperidin]-1'-yl)-3-(3-fluorophenoxy)propan-2-ol,
(2S)-1-(5-Chloro-1'H,3H-spiro[1-benzofuran-2,4'-piperidin]-1'-yl)-3-(4-fluorophenoxy)propan-2-ol,
(2S)-1-(2-Chlorophenoxy)-3-(5-chloro-1'H,3H-spiro[1-benzofuran-2,4'-piperidin]-1'-yl)propan-2-ol,
(2S)-1-(3-Chlorophenoxy)-3-(5-chloro-1'H,3H-spiro[1-benzofuran-2,4'-piperidin]-1'-yl)propan-2-ol,
(2S)-1-(4-Chlorophenoxy)-3-(5-chloro-1'H,3H-spiro[1-benzofuran-2,4'-piperidin]-1'-yl)propan-2-ol,
(2S)-1-(3-Bromophenoxy)-3-(5-chloro-1'H,3H-spiro[1-benzofuran-2,4'-piperidin]-1'-yl)propan-2-ol,
(2S)-1-(4-Bromophenoxy)-3-(5-chloro-1'H,3H-spiro[1-benzofuran-2,4'-piperidin]-1'-yl)propan-2-ol,
(2S)-1-(2-tert-Butyl-5-methylphenoxy)-3-(5-chloro-1'H,3H-spiro[1-benzofuran-2,4'-piperidin]-1'-yl)propan-2-ol,
(2S)-1-(5-Chloro-1'H,3H-spiro[1-benzofuran-2,4'-piperidin]-1'-yl)-3-[2-(trifluoromethyl)phenoxy]propan-2-ol,
1-(2-{[(2S)-3-(5-Chloro-1'H,3H-spiro[1-benzofuran-2,4'-piperidin]-1'-yl)-2-hydroxypropyl]oxy}-4,5-dimethoxyphenyl)ethanone,
(2S)-1-(5-Chloro-1'H,3H-spiro[1-benzofuran-2,4'-piperidin]-1'-yl)-3-[2,3,5,6-tetrafluoro-4-(trifluoromethyl)phenoxy]propan-2-ol,
(2S)-1-(4-Chloro-3-ethylphenoxy)-3-(5-chloro-1'H,3H-spiro[1-benzofuran-2,4'-piperidin]-1'-yl)propan-2-ol,
(2S)-1-(5-Chloro-1'H,3H-spiro[1-benzofuran-2,4'-piperidin]-1'-yl)-3-[3-(2,5-dimethyl-1H-pyrol-1-yl)phenoxy]propan-2-ol,
(2S)-1-(5-Chloro-1'H,3H-spiro[1-benzofuran-2,4'-piperidin]-1'-yl)-3-[2-(hydroxymethyl)phenoxy]propan-2-ol,
(2S)-1-(5-Chloro-1'H,3H-spiro[1-benzofuran-2,4'-piperidin]-1'-yl)-3-[2-(2-hydroxyethyl)phenoxy]propan-2-ol,
3-{[(2S)-3-(5-Chloro-1'H,3H-spiro[1-benzofuran-2,4'-piperidin]-1'-yl)-2-hydroxypropyl]oxy}benzonitrile,
2-{[(2S)-3-(5-Chloro-1'H,3H-spiro[1-benzofuran-2,4'-piperidin]-1'-yl)-2-hydroxypropyl]oxy}benzonitrile,
(2S)-1-(5-Chloro-1'H,3H-spiro[1-benzofuran-2,4'-piperidin]-1'-yl)-3-(2-morpholin-4-ylphenoxy)propan-2-ol,
(2S)-1-(5-Chloro-1'H,3H-spiro[1-benzofuran-2,4'-piperidin]-1'-yl)-3-(2,3-difluoro-6-nitrophenoxy)propan-2-ol,
(2S)-1-(5-Chloro-1'H,3H-spiro[1-benzofuran-2,4'-piperidin]-1'-yl)-3-(2,3,6-trichlorophenoxy)propan-2-ol,
(2S)-1-(5-Chloro-1'H,3H-spiro[1-benzofuran-2,4'-piperidin]-1'-yl)-3-(4-fluoro-2-methoxyphenoxy)propan-2-ol,
5-Chloro-2-{[(2S)-3-(5-chloro-1'H,3H-spiro[1-benzofuran-2,4'-piperidin]-1'-yl)-2-hydroxypropyl]oxy}-3-methylbenzaldehyde,
(2S)-1-(5-Chloro-1'H,3H-spiro[1-benzofuran-2,4'-piperidin]-1'-yl)-3-[4-(4-methylpiperidin-1-yl)-2-nitrophenoxy]propan-2-ol,
(2S)-1-(5-Chloro-1'H,3H-spiro[1-benzofuran-2,4'-piperidin]-1'-yl)-3-(2,4-dichloro-3,5-dimethyl-6-nitrophenoxy)propan-2-ol,
1-(3,5-Dichloro-2-{[(2S)-3-(5-chloro-1'H,3H-spiro[1-benzofuran-2,4'-piperidin]-1'-yl)-2-hydroxypropyl]oxy}phenyl)propan-1-one,
(2S)-1-(5-Chloro-1'H,3H-spiro[1-benzofuran-2,4'-piperidin]-1'-yl)-3-(4-ethylphenoxy)propan-2-ol,
(2S)-1-(5-Chloro-1'H,3H-spiro[1-benzofuran-2,4'-piperidin]-1'-yl)-3-(2-ethylphenoxy)propan-2-ol,
(2S)-1-(5-Chloro-1'H,3H-spiro[1-benzofuran-2,4'-piperidin]-1'-yl)-3-(3-ethylphenoxy)propan-2-ol,
(2S)-1-(5-Chloro-1'H,3H-spiro[1-benzofuran-2,4'-piperidin]-1'-yl)-3-(3-morpholin-4-ylphenoxy)propan-2-ol,
(2S)-1-(5-Chloro-1'H,3H-spiro[1-benzofuran-2,4'-piperidin]-1'-yl)-3-[2-(5-methyl-1,3,4-oxadiazol-2-yl)phenoxy]propan-2-ol,
4-{[(2S)-3-(5-Chloro-1'H,3H-spiro[1-benzofuran-2,4'-piperidin]-1'-yl)-2-hydroxypropyl]oxy}benzonitrile,
(2S)-1-(5-chloro-1'H,3H-spiro[1-benzofuran-2,4'-piperidin]-1'-yl)-3-[2-(pyrrolidin-1-ylsulfonyl)phenoxy]propan-2-ol.
1-(2-{[(2S)-3-(5-chloro-1'H,3H-spiro[1-benzofuran-2,4'-piperidin]-1'-yl)-2-hydroxypropoxy]benzyl}imidazoline-2,4-dione,
(2S)-{2-chloro-5-[3-(5-chloro-1'H,3H-spiro[1-benzofuran-2,4'-piperidin]-1'-yl)-2-hydroxypropoxy]phenoxy}acetic acid,
(2S)-{2,4-dichloro-5-[3-(5-chloro-1'H,3H-spiro[1-benzofuran-2,4'-piperidin]-1'-yl)-2-hydroxypropoxy]phenoxy}acetic acid, and pharmaceutically acceptable salts of any one thereof.

9. A process for the preparation of a compound of formula (I) or a pharmaceutically acceptable salt thereof as defined in claim 1 which comprises,
(a) reacting a compound of formula

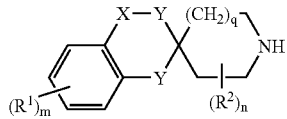
(II)

wherein m, $R^1$, n, $R^2$, q, X, Y and Z are as defined in formula (I), with a compound of formula

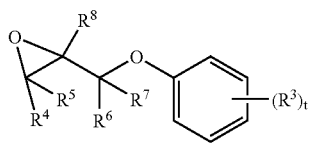
(III)

wherein t, $R^3$, $R^4$, $R^5$, $R^6$, $R^7$ and $R^8$ are as defined in formula (I); or
(b) reacting a compound of formula

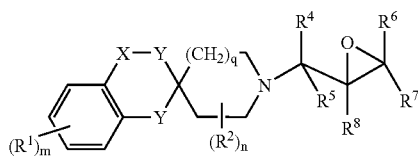
(IV)

wherein m, $R^1$, n, $R^2$, q, X, Y, Z, $R^4$, $R^5$, $R^6$, $R^7$ and $R^8$ are as defined in formula (I), with a compound of formula

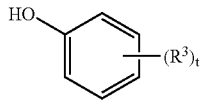
(V)

wherein t and $R^3$ are as defined in formula (I), in the presence of a suitable base; or
(c) when t is at least one and a group $R^3$ represents —$NHSO_2R^{14}$, reacting a compound of formula

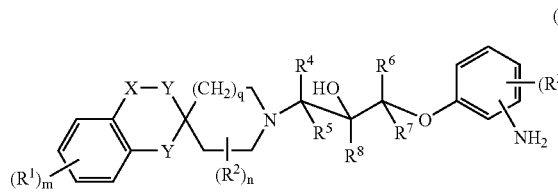
(VI)

wherein t' is 0, 1, 2, 3 or 4, $R^{3'}$ is as defined for $R^3$ in formula (I) other than —$NHSO_2R^{14}$ and m, $R^1$, n, $R^2$, q, X, Y, Z, $R^4$, $R^5$, $R^6$, $R^7$ and $R^8$ are as defined in formula (I), with a compound of formula

(VII)

wherein L represents a leaving group and $R^{14}$ is as defined in formula (I), in the presence of a suitable base;
(d) where t is at least 1 and a group $R^3$ represents —$CH_2$—R17, where R17 is a 5 to 7-membered saturated heterocyclic ring containing 2 nitrogen atoms and which ring is substituted by two oxo groups, reacting a compound of formula

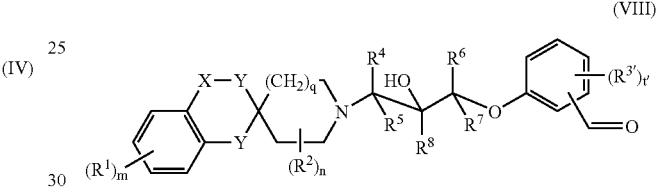
(VIII)

wherein t' is 0, 1, 2, 3 or 4, $R^{3'}$ is as defined for $R^3$ in formula (I) other than —CH2-$R^{17}$, and m, $R^1$, n, $R^2$, q, X, Y, Z, $R^4$, $R^5$, $R^6$, $R^7$ and $R^8$ are as defined in formula (I), with an alkyl glycinate in the presence of a reducing agent, and subsequently with metal isocyanate;
and optionally after (a), (b) or (c) forming a pharmaceutically acceptable salt.

10. A pharmaceutical composition comprising a compound of formula (I) or a pharmaceutically acceptable salt thereof as claimed in claim 1 in association with a pharmaceutically acceptable adjuvant, diluent or carrier.

11. A process for the preparation of a pharmaceutical composition comprising a compound of formula (I) or a pharmaceutically acceptable salt thereof as claimed in claim 1 in association with a pharmaceutically acceptable adjuvant, diluent or carrier, which comprises mixing a compound of formula (I) or a pharmaceutically acceptable salt thereof as claimed in claim 1 with a pharmaceutically acceptable adjuvant, diluent or carrier.

* * * * *